(12) United States Patent
Tomlin et al.

(10) Patent No.: US 10,134,192 B2
(45) Date of Patent: Nov. 20, 2018

(54) GENERATING AND DISPLAYING A COMPUTER GENERATED IMAGE ON A FUTURE POSE OF A REAL WORLD OBJECT

(71) Applicant: MICROSOFT TECHNOLOGY LICENSING, LLC, Redmond, WA (US)

(72) Inventors: Arthur Tomlin, Kirkland, WA (US); Adam Gabriel Poulos, Sammamish, WA (US); Cameron Graeme Brown, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 15/295,791

(22) Filed: Oct. 17, 2016

(65) Prior Publication Data

US 2018/0108179 A1    Apr. 19, 2018

(51) Int. Cl.
*G06T 19/00*    (2011.01)
*G06F 1/14*    (2006.01)
(Continued)

(52) U.S. Cl.
CPC ........ *G06T 19/006* (2013.01); *G02B 27/0172* (2013.01); *G06F 1/14* (2013.01);
(Continued)

(58) Field of Classification Search
CPC .................................................. G06T 19/006
(Continued)

(56) References Cited

U.S. PATENT DOCUMENTS 8,472,703 B2    6/2013    Takemoto et al.
8,854,282 B1    10/2014    Wong
(Continued)

FOREIGN PATENT DOCUMENTS

EP    1336916 A2    8/2003
WO    2014100093 A1    6/2014
(Continued)

OTHER PUBLICATIONS

Foxlin, et al., "Miniature 6-DOF inertial system for tracking HMDs", In Proceedings of the SPIE, vol. 3362, Apr. 13, 1998, pp. 1-15.
(Continued)

*Primary Examiner* — Javid A Amini
(74) *Attorney, Agent, or Firm* — Workman Nydegger

(57) ABSTRACT

Methods and systems for displaying a computer generated image corresponding to the pose of a real-world object in a mixed reality system. The system may include of a head-mounted display (HMD) device, a magnetic track system and an optical system. Pose data detected by the two tracking systems can be synchronized by a timestamp that is embedded in an electromagnetic field transmitted by the magnetic tracking system. A processor may also be configured to calculate a future pose of the real world object based on a time offset based on the time needed by the HMD to calculate, buffer and generate display output and on data from the two tracking systems, such that the relative location of the computer generated image (CGI) corresponds with the actual location of the real-world object relative to the real world environment at the time the CGI actually appears in the display.

21 Claims, 18 Drawing Sheets

(51) Int. Cl.
   *G06F 3/03* (2006.01)
   *G02B 27/01* (2006.01)
   *G06F 3/01* (2006.01)
   *G06F 3/0346* (2013.01)
   *G06T 7/00* (2017.01)
   *A61B 90/00* (2016.01)

(52) U.S. Cl.
   CPC ............ *G06F 3/012* (2013.01); *G06F 3/0304* (2013.01); *G06F 3/0346* (2013.01); *A61B 2090/365* (2016.02); *G02B 2027/014* (2013.01); *G06T 7/004* (2013.01)

(58) Field of Classification Search
   USPC ........................................................ 345/633
   See application file for complete search history.

(56) References Cited

U.S. PATENT DOCUMENTS

| | | | |
|---|---|---|---|
| 8,965,741 B2 | 2/2015 | McCulloch et al. | |
| 9,035,955 B2 | 5/2015 | Keane et al. | |
| 9,141,194 B1 | 9/2015 | Keyes et al. | |
| 9,250,443 B2 | 2/2016 | Park et al. | |
| 2002/0196343 A1* | 12/2002 | Navab | H04N 7/18 348/169 |
| 2003/0025714 A1* | 2/2003 | Ebersole | G06F 3/011 345/632 |
| 2004/0036717 A1* | 2/2004 | Kjeldsen | G03B 21/28 715/730 |
| 2004/0149036 A1* | 8/2004 | Foxlin | A61B 5/1113 73/511 |
| 2008/0167814 A1* | 7/2008 | Samarasekera | G01C 21/005 701/469 |
| 2009/0180668 A1* | 7/2009 | Jones | G06F 3/017 382/103 |
| 2010/0197390 A1* | 8/2010 | Craig | G06K 9/00369 463/30 |
| 2010/0259471 A1 | 10/2010 | Takano et al. | |
| 2011/0267269 A1* | 11/2011 | Tardif | G06F 3/011 345/158 |
| 2013/0169626 A1 | 7/2013 | Balan et al. | |
| 2013/0174213 A1 | 7/2013 | Liu et al. | |
| 2014/0176591 A1* | 6/2014 | Klein | G09G 3/003 345/589 |
| 2014/0293748 A1 | 10/2014 | Altman et al. | |
| 2014/0333666 A1* | 11/2014 | Poulos | G06T 19/006 345/633 |
| 2014/0368535 A1* | 12/2014 | Salter | G02B 27/017 345/619 |
| 2014/0369557 A1* | 12/2014 | Kayombya | G06K 9/00624 382/103 |
| 2016/0033768 A1 | 2/2016 | Pedrotti et al. | |
| 2016/0052451 A1* | 2/2016 | O'Kane | B60Q 9/008 340/435 |
| 2016/0063708 A1* | 3/2016 | Okuyan | G06T 7/0042 382/103 |
| 2016/0171860 A1* | 6/2016 | Hannigan | G08B 21/02 340/686.1 |
| 2016/0219208 A1* | 7/2016 | Horesh | H04N 5/23219 |
| 2016/0259404 A1 | 9/2016 | Woods | |
| 2016/0300391 A1* | 10/2016 | Whittinghill | A63F 13/803 |
| 2017/0205903 A1* | 7/2017 | Miller | G06F 3/0346 |
| 2017/0316333 A1* | 11/2017 | Levinson | G06N 99/005 |

FOREIGN PATENT DOCUMENTS

| | | |
|---|---|---|
| WO | 2016032678 A1 | 3/2016 |
| WO | 2016041088 A1 | 3/2016 |

OTHER PUBLICATIONS

"International Search Report and Written Opinion Issued in PCT Application No. PCT/US2017/055681", dated Dec. 13, 2017, 10 Pages.

* cited by examiner

GENERATING AND DISPLAYING A COMPUTER GENERATED IMAGE ON A FUTURE POSE OF A REAL WORLD OBJECT

BACKGROUND

Recently, various technologies have emerged that allow users to experience a blend of reality and virtual worlds along a mixed reality continuum. For example, head-mounted display (HMD) devices may include various sensors that allow the HMD device to display a blend of reality and virtual objects on the HMD device as augmented reality, or block out the real world view to display only virtual reality. Whether for virtual or augmented reality, a closer tie between real-world features and the display of virtual objects is often desired in order to heighten the interactive experience and provide the user with more control.

One way to bring real-world features into the virtual world is to track a handheld controller through space as it is being used. However, some conventional controllers lack precise resolution and users end up with choppy, inaccurate display of the virtual objects. Some handheld controllers even require externally positioned cameras, tethering use of the HMD device to a small area. Similarly, some physical object tracking systems use stationary transmitters with a short transmission range, also tethering the user to a small area. Further, these physical object tracking systems often experience signal degradation toward the limits of the transmission range in addition to interference from other objects and energy sources in the environment. In the face of such degradation, the accuracy of the tracking system can become completely unreliable under various circumstances, which negatively impacts the interactive experience for the user. Further still, they often report position within one zone at a time, which can lead to problems when the object is moved between zones while temporarily located beyond the range of the tracking system.

BRIEF SUMMARY

One embodiment illustrated herein includes a system for displaying a computer generated image corresponding to the pose of a real-world object in a mixed reality system. The system may comprise a head-mounted display (HMD) device that includes a display rendering system having a time offset based on the time needed to calculate, buffer and generate display output. The system may also comprise a magnetic tracking system configured to detect the pose of the object where the magnetic tracking system includes a base station configured to emit an electromagnetic field (EMF) and an EMF sensor configured to sense the EMF. The system may further comprise a second tracking system configured to also detect the pose of the object. In an embodiment, the data derived from the magnetic tracking system and the data derived from the second tracking system may be synchronized in time. The system may comprise a processor configured to calculate a future pose of the real world object based in part on the time offset, pose, velocity and acceleration from the magnetic tracking system, and the time offset, pose, velocity and acceleration from the second tracking system, such that the relative location of the computer generated image (CGI) corresponds with the actual location of the real-world object relative to the real world environment at the time the CGI actually appears in the mixed reality display.

BRIEF DESCRIPTION OF THE DRAWINGS

To describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Some embodiments herein implement a solution that allow a mixed reality system to fuse data from two or more tracking systems to determine the location, orientation, velocity, and acceleration of a real-world object. In one embodiment, a system for displaying a computer generated image corresponding to the pose of a real-world object in a mixed reality system. The system may comprise a head-mounted display (HMD) device. The system may further comprise a magnetic tracking system configured to detect the pose of the object, the magnetic tracking system comprising a base station configured to emit an electromagnetic field (EMF) and an EMF sensor configured to sense the EMF. The system may further comprise a second tracking system configured to detect the pose of the object. The data derived from the magnetic tracking system and the data derived from the second tracking system may be synchronized in time.

An alternate embodiment implements a solution to enable a mixed reality system to display a computer generated virtual object corresponding to the location and orientation of a tracked real-world object in a mixed reality system. The system may comprise a head-mounted display (HMD) device that includes a display rendering system having a time offset based on the time needed to calculate, buffer and generate display output. The system may further comprise a first tracking system configured to detect pose, velocity and acceleration of the real world object. The system may comprise a second tracking system configured to detect pose, velocity and acceleration of the real world object. The system may also comprise a processor configured to calculate a future pose of the real world object based in part on the time offset, pose, velocity and acceleration data from the first tracking system, and the time offset, pose, velocity and acceleration data from the second tracking system, such that the relative location of the computer generated image (CGI) corresponds with the actual location of the real-world object relative to the real world environment at the time the CGI actually appears in the mixed reality display.

Figure 1:
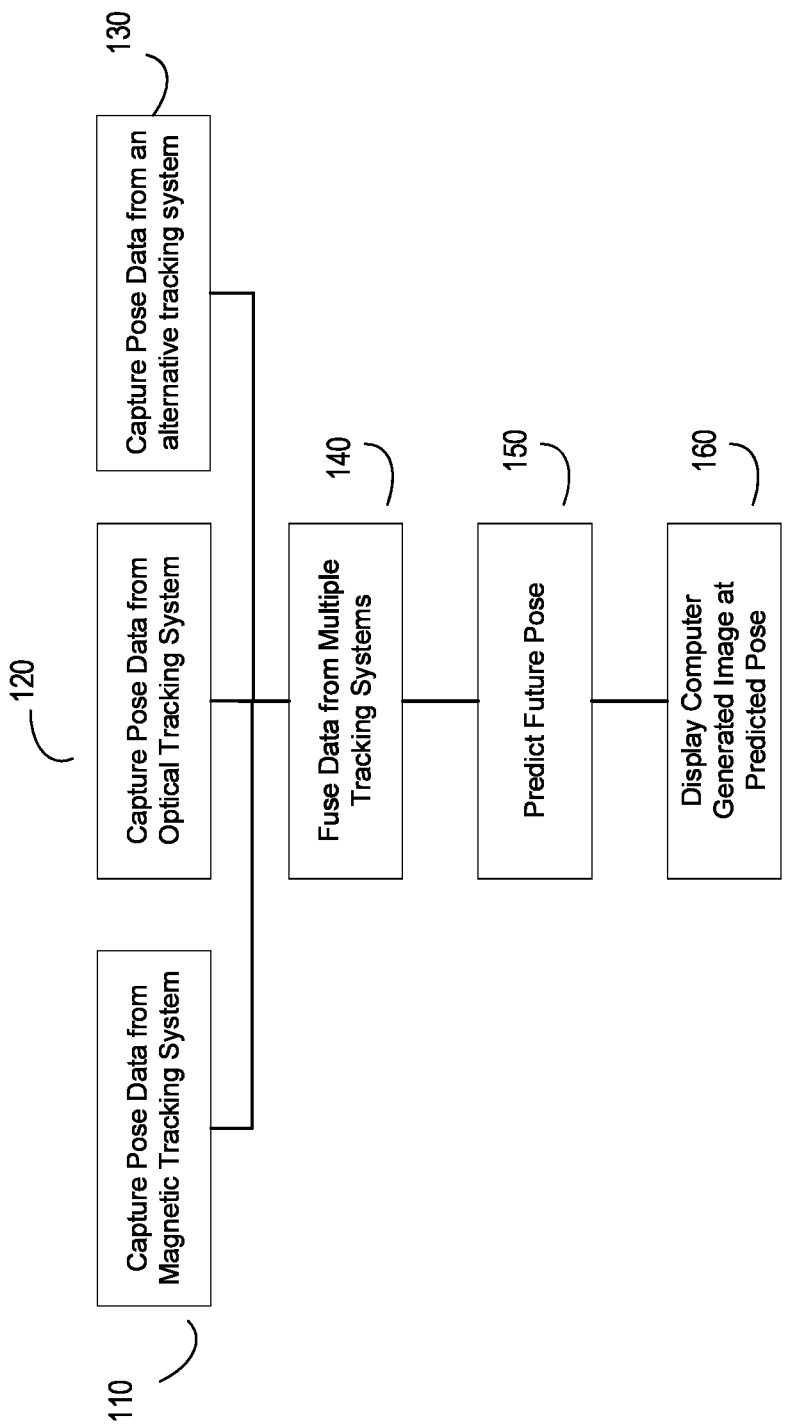
FIG. 1 illustrates a flowchart for a method to display a computer generated image (CGI) at a future pose.

FIG. 1 illustrates an exemplary flowchart to provide an overview of a mixed reality system 100 (described later) to display computer generated images (CGI) on objects in the real-world. A magnetic tracking system will capture pose data (act 110) for one or more objects in the real-world. In addition, an optical tracking system (act 120) and/or an alternative tracking system (act 130) will capture independent pose data for the same one or more objects in the real-world. As used herein, a "pose" may include position and orientation for a total of six values per location (e.g. X, Y, Z for position and pitch, roll, yaw for orientation). The data set from each tracking system is captured and may be shared with a processor. Since each tracking system may have inherent differences and latencies, the timing of when the pose data is received by the processor may differ between tracking systems. The independent pose data sets may be synchronized, or fused, by time so that a highly accurate pose, velocity, and acceleration can be determined for that moment in time (act 140). Based on the collection of pose data, a future pose for the real-world object can be predicted (i.e. a predicted pose of the real-world object at an expected time in the future) by factoring in the pose, velocity and acceleration of the one or more real-world objects, the time delay of the tracking systems (i.e. factoring in past data), and the predicted time required to create, buffer, and display the CGI (i.e. an anticipated time delay to render the CGI) (act 150). The CGI may then be created, buffered, and displayed to the user of the mixed reality system for that future point in time and for the predicted pose so that the CGI and the real-world object are aligned in pose from the viewing perspective of the mixed reality system at each moment in time (act 160).

Figure 2:
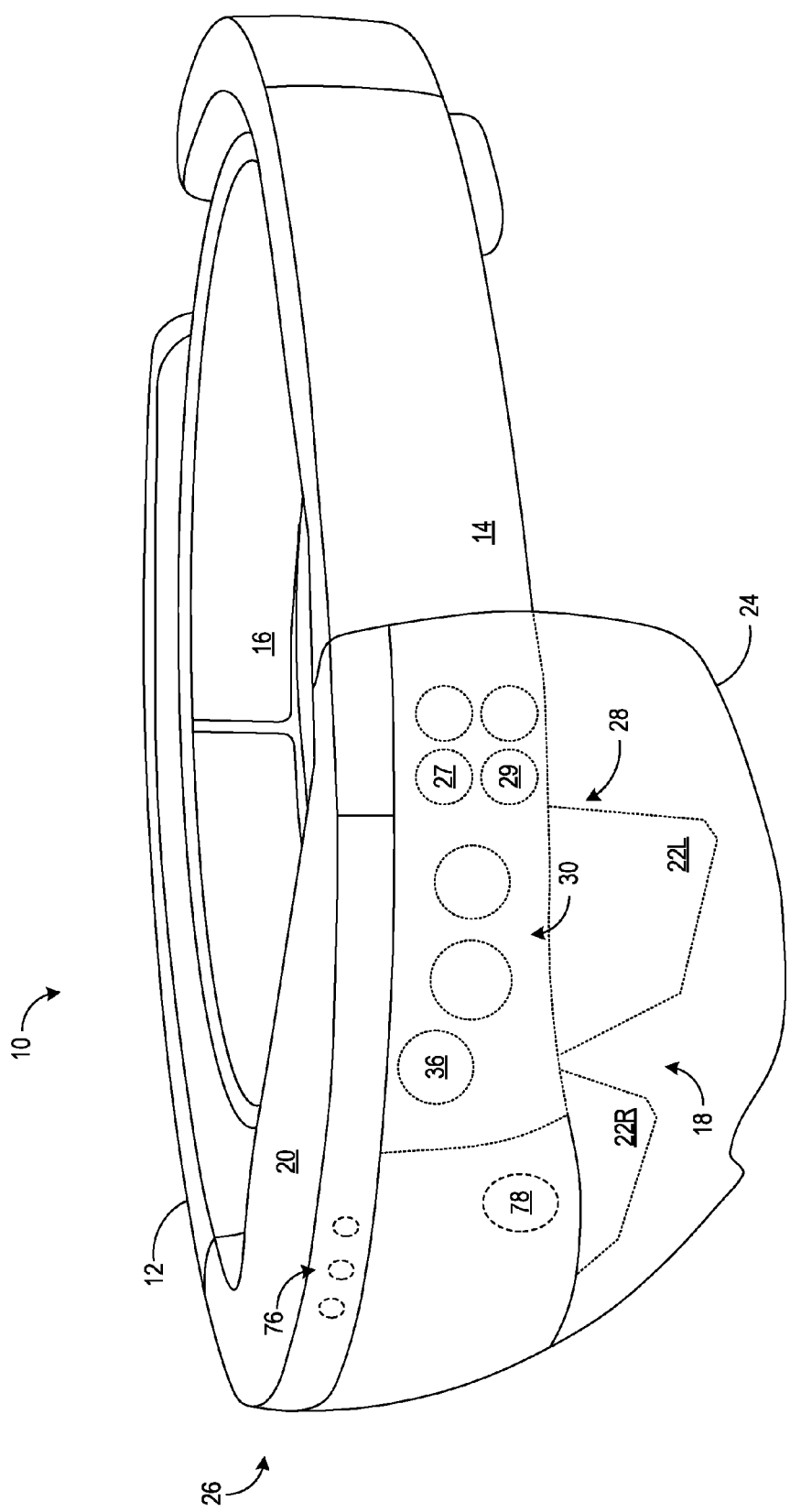
FIG. 2 shows a schematic of a head-mounted display (HMD) device.

FIG. 2 shows a schematic illustration of a head-mounted display (HMD) device 10, which may be part of a mixed reality system 100 (described later). The illustrated HMD device 10 takes the form of a wearable visor, but it will be appreciated that other forms are possible, such as glasses or goggles, among others. The HMD device 10 may include a housing 12 including a band 14 and an inner band 16 to rest on a user's head. The HMD device 10 may include a display 18 which is controlled by a controller 20. The display 18 may be a stereoscopic display and may include a left panel 22L and a right panel 22R as shown, or alternatively, a single panel of a suitable shape. The panels 22L, 22R are not limited to the shape shown and may be, for example, round, oval, square, or other shapes including lens-shaped. The HMD device 10 may also include a shield 24 attached to a front portion 26 of the housing 12 of the HMD device 10. The display 18 and/or the shield 24 may include one or more regions that are transparent, opaque, or semi-transparent. Any of these portions may further be configured to change transparency by suitable means. As such, the HMD device 10 may be suited for both augmented reality situations and virtual reality situations.

The HMD device 10 may comprise a position sensor system 28 which may include one or more sensors such as optical sensor(s) like depth camera(s) RGB camera(s), accelerometer(s), gyroscope(s), magnetometer(s), global positioning system(s) (GPSs), multilateration tracker(s), and/or other sensors that output position sensor information useable to extract a position (e.g. X, Y, Z), orientation (e.g. pitch, roll, yaw), and/or movement of the relevant sensor. Of these, the position sensor system 28 may include one or more location sensor 30 from which the HMD device 10 determines a location 62 (see FIG. 2) of the location sensor 30 in space. As used herein, a "location" may be a "pose" and may include position and orientation for a total of six values per location. For example, the location sensor 30 may be at least one camera, and as depicted, may be a camera cluster. The position sensor system 28 is also shown as including at least an accelerometer 27 and gyroscope 29. In another example, the HMD device 10 may determine the location of the location sensor 30 by receiving a calculated location from an externally positioned locating system that calculates the location of the HMD device 10 as the location of the location sensor 30. The HMD may include at least one optical sensor 78.

Figure 3:
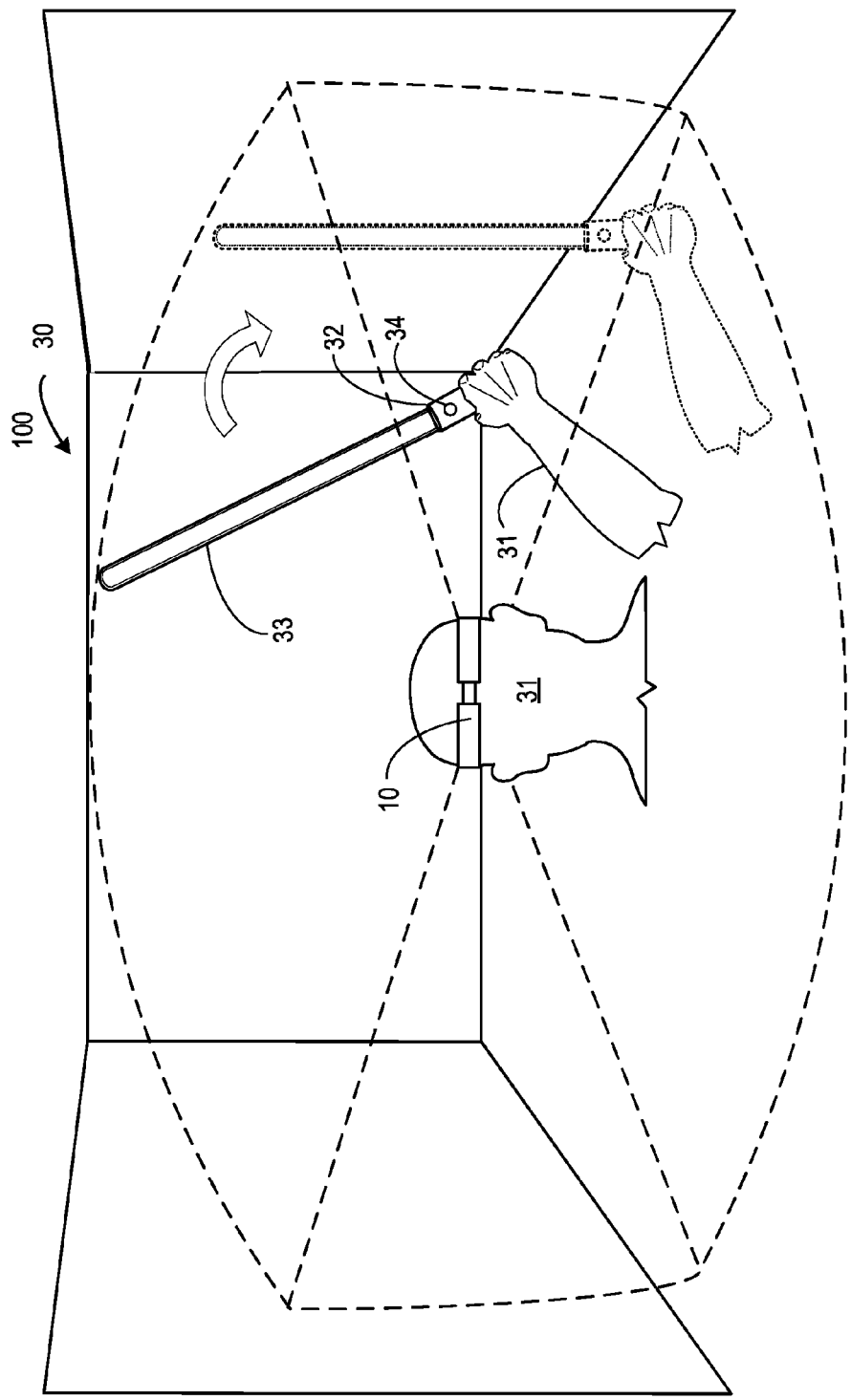
FIG. 3 shows an example augmented reality situation of the mixed reality system.

FIG. 3 shows an example augmented reality situation of the mixed reality system 100. As discussed above with reference to FIG. 2, the HMD device 10 may comprise the display 18 which may be an at least partially see-through display configured to display augmented reality images, which may be controlled by the controller 20. In the example shown, the real-world object may be a handheld input device 32 such as a video game controller configured to provide user input to the HMD device 10. To provide such functionality, the handheld input device 32 may comprise its own processor, memory, and transceiver, among other components, discussed below with reference to FIG. 10. The handheld input device 32 may also comprise one or more input controls 34 such as a button, trigger, joystick, directional pad, touch screen, accelerometer, gyroscope, etc.

In the example of FIG. 3, a user 31 may view an augmented reality scene with the HMD device 10, shown here in dashed lines. The user 31 may hold the handheld input device 32 with his hand and move the handheld input device 32 over time from a first position, shown in solid lines, to a second position, shown in dotted lines. By tracking the pose (described later) of the handheld input device 32, the display 18 may be further configured to overlay a hologram 33 that corresponds to the pose of the handheld input device 32 in space over time. In this example, the hologram 33 may be a glowing sword which incorporates the real handheld input device 32 as a hilt and follows the handheld input device 32 as it is waved around in space by the user 31. When rendering the virtual or augmented reality image, the mixed reality system 100 may experience increased accuracy and decreased latency compared to other HMD devices that use, for example, external cameras to locate objects. Furthermore, the depicted user 31 is free to move to other areas while continuing to wear and operate the HMD device 10 without disrupting the current use session or losing track of the handheld input device 32.

Figure 4:
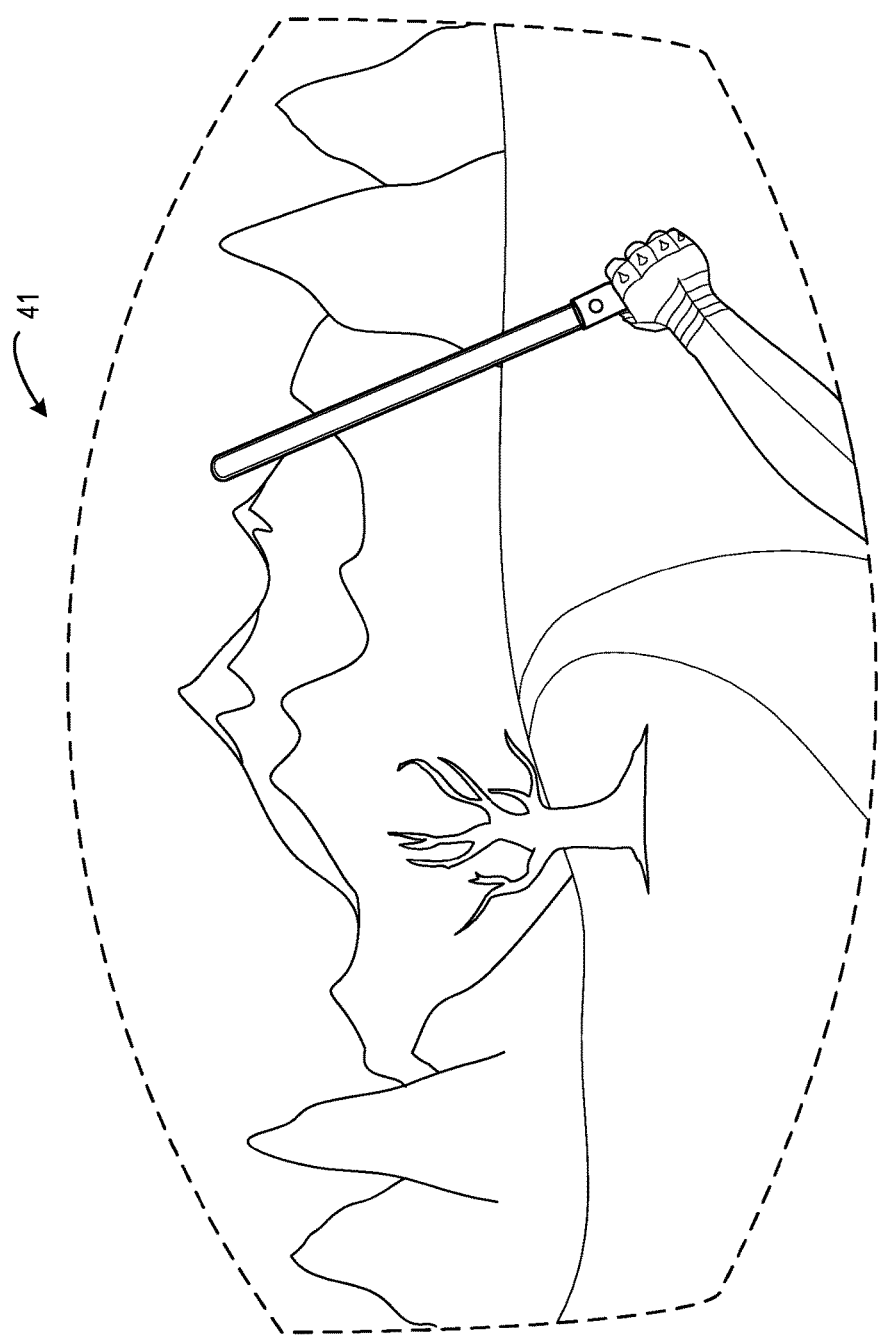
FIG. 4 shows an example virtual reality situation of the mixed reality system.

FIG. 4 shows an example virtual reality situation of the mixed reality system 100, similar to the augmented reality situation discussed above. As discussed above, the HMD device 10 may comprise the display 18 which may be an at least partially opaque display configured to display virtual reality images 41, and may further be a multimodal display which is configured to switch to an opaque, virtual reality mode. As above, the display 18 may be controlled by the handheld input device 32. Rather than the hologram 33 in the augmented reality situation above, FIG. 4 shows virtual reality images 41 such as a tree and mountains in the background, a gauntlet which corresponds to the user's hand, and the glowing sword which moves together with the handheld input device 32 in the real world.

A) Capture Pose Data from a Magnetic Tracking System

Figure 5:
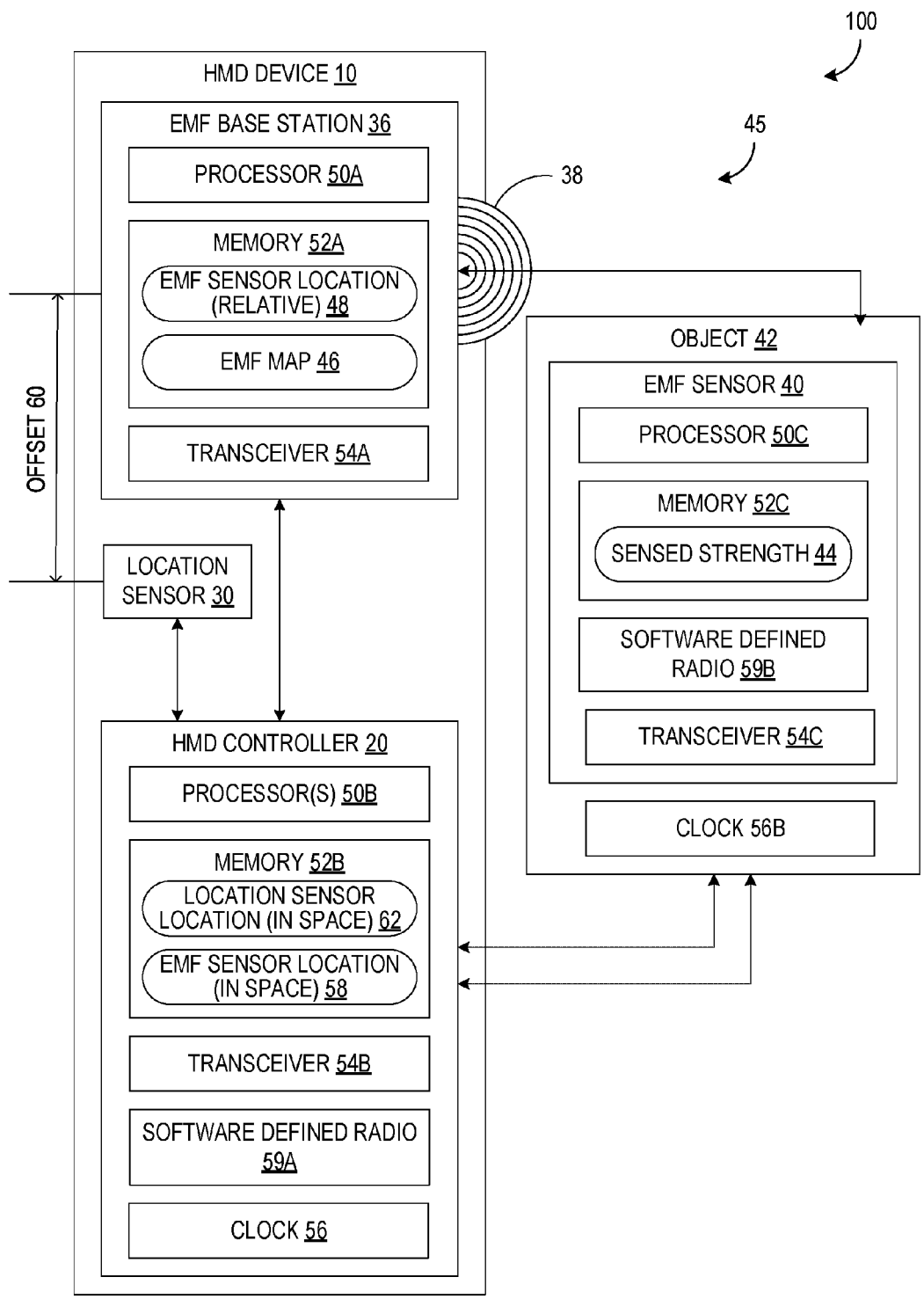
FIG. 5 shows an example software-hardware diagram of a mixed reality system including the HMD device.

Referring to FIG. 1, the HMD device 10 may include an electromagnetic tracking system to track a real world object and capture data corresponding to the pose of the real world object (act 110). Referring to FIG. 5, the magnetic tracking system 45 may comprise a base station that emits an electromagnetic field (EMF) and one or more sensors to detect the EMF.

FIG. 5 shows an example software-hardware diagram of the mixed reality system 100 including the HMD device 10. In addition to the HMD device 10, the mixed reality system 100 may also include an electromagnetic field sensor 40 affixed to an object 42 and configured to sense a strength 44 of the electromagnetic field 38. The electromagnetic field sensor 40 may be incorporated into the object 42 or may be in the form of a removably mountable sensor which may be temporarily affixed to the object 42 via adhesives, fasteners, etc., such that the object 42 being tracked may be swapped out and may thus be a wide variety of objects. The base station 36 and the electromagnetic field sensor 40 together may form a magnetic tracking system 45. It will be appreciated that each of the base station 36 and the electromagnetic field sensor 40 may include several embodiments to experience a respective magnetic flux. Embodiments may include three orthogonal coils or four coils in a tetrahedral form. As another embodiment, two transmitter coils and three receiver coils in combination with a second tracking system to disambiguate pose coordinates may be used.

The electromagnetic field 38 may propagate in all directions, and may be blocked or otherwise affected by various materials, such as metals, or energy sources, etc. When the base station 36 is rigidly supported at a fixed location relative to the HMD device 10, components of the HMD device 10 which are known to cause interference may be accounted for by generating an electromagnetic field map 46 of various sensed strengths 44, each measured at a known relative location 48. Furthermore, when the base station 36 is positioned in the front portion 26 of the housing 12, fewer sources of interference may be present between the base station 36 and the electromagnetic field sensor 40, and when the user of the HMD device 10 is holding or looking at the object 42, then the range of the base station 36 may be utilized to its full potential by positioning the base station 36 in front of the user at all times.

The base station 36 may include a processor 50A configured to execute instructions stored in memory 52A and a transceiver 54A that allows the base station to communicate with the electromagnetic field sensor 40 and/or controller 20. The base station 36 may also be configured to communicate over a wired connection, which may decrease latency in the mixed reality system 100. The controller 20 may include one or more processors 50B configured to execute instructions stored in memory 52B and a transceiver 54B that allows the controller to communicate with the electromagnetic field sensor 40, the base station 36, and/or other devices. Further, the electromagnetic field sensor 40 may include a processor 50C configured to execute instructions stored in memory 52C and a transceiver 54C that allows the electromagnetic field sensor 40 to wirelessly communicate with the base station 36 and/or controller 20. Wireless communication may occur over, for example, WI-FI, BLUETOOTH, or a custom wireless protocol. It will be appreciated that a transceiver may comprise one or more combined or separate receiver and transmitter.

The HMD device 10 may include a processor, which may be the processor 50A or the processor 50B, configured to determine a relative location 48 of the electromagnetic field sensor 40 relative to the base station 36 based on the sensed strength 44. The processor may be configured to determine a location 58 of the electromagnetic field sensor 40 in space based on the relative location 48, the predetermined offset 60, and the location 62 of the location sensor 30 in space. If the location sensor is a camera, for example, the camera may be configured to send the controller 20 one or more images from which the controller may, via image recognition, determine the location of the location sensor 30 in space. If the location sensor is a GPS receiver paired with an accelerometer, as another example, then the location 62 of the location sensor 30 may be determined by receiving the position from the GPS receiver and the orientation may be determined by the accelerometer. In one case, the electromagnetic field sensor 40 may be configured to communicate the sensed strength 44 to the base station 36 or the controller 20, and the base station 36 or controller 20 may be configured to determine the relative location 48 of the electromagnetic field sensor 40 relative to the base station 36 based on the sensed strength 44. Alternatively, the processor 50C of the electromagnetic field sensor 40 may be configured to determine the relative location 48 of the electromagnetic field sensor 40 relative to the base station 36 based on the sensed strength 44 and communicate the relative location 48 of the electromagnetic field sensor 40 relative to the base station 36, to the base station 36 or controller 20. In the former case, the HMD device 10 may lower a processing burden of the electromagnetic field sensor 40 by determining the relative location 48 itself, while in the latter case, performing the relative location determination processing or even some pre-processing at the electromagnetic field sensor 40 may lower a communication burden of the electromagnetic field sensor 40.

The electromagnetic field map 46 which correlates the known pattern of the electromagnetic field 38 emitted by the base station 36 to the sensed strength 44 at various relative locations within the range of the base station 36 may be stored in the memory 52A, 52B, and/or 52C.

The strength of the electromagnetic field 38 of the magnetic tracking system 45 may be optimized for the targeted mixed reality system 100. The strength of an electromagnetic field will diminish at an inversed cube rate to the distance from the base station (i.e. $1/r^3$). For example, the signal strength for the EMF base station 36 may be preconfigured at the factory for a HMD 10 and a hand-held input device 32 based on an expected radius of one meter. When a larger radius is required by the mixed reality system 100, the power used by the base station to create the electromagnetic field 38 can be increased proportionally. In an embodiment, the processor 50A, 50B or 50C may be configured to adjust the signal strength of the EMF base station 36 based on the detected signal strength 44 falling above or below a prescribed range. The prescribed signal strength range may in part be determined by a threshold of an expected signal to noise ratio from the electromagnetic field 44. For example, when the noise ratio exceeds the defined level, the processor 50A, 50B or 50C may increase the power of the electromagnetic signal 44 by the EMF base station 36 to improve the signal strength and thereby reducing the noise ratio.

The HMD device 10 may include a software defined radio (SDR) 59A or 59B to process the signal received from the electromagnetic field sensor 40. The SDR 59A may be configured to the HMD 10 to receive, store, and/or analyze the EMF signal at the rate of the actual magnetic frequency. The SDR 59 may alternatively, or additionally, receive, record, and/or analyze the EMF signal in a reduced frequency where the analog signal is averaged over a prescribed period. Alternatively, the SDR 59 may sample the data at a calculated rate, for example two milliseconds. As an example, the calculation may be determined by a rate of change observed in the object. In such a case, when the rate of change increases the number of samples would increase. The SDR may be further configured to process the signal at more than one frequency thus providing multiple data sets for the received EMF signal over time. For example, a first data set may average EMF signal ten times each millisecond and a second data set may average the same EMF signal every two milliseconds. Alternatively, the SDR 59B may be configured to the object 42 to process the signal received from the EMF sensor 40.

In order to synchronize measurements performed by the pair of the electromagnetic field sensor 40 and the base station 36 with measurements performed by the location sensor 30, the inertial measurement unit (IMU) 96, and/or other tracking system, the controller 20 may include a common clock 56 to provide timestamps for data reporting from multiple sources. The electromagnetic field 38 emitted may be modulated by the base station 36 so that the time from the common clock 56 is embedded in the electromagnetic signal. An alternative embodiment may use a fixed time delay determined by known hardware and software latencies to synchronize the measurements. Alternatively, an algorithm may be used to synchronize two or more clocks. For example, Processor 50B may use common clock 56 and an algorithm to synchronize the time on the processor 50C and the object's clock 56B. As an alternative example, the synchronization of clocks may be switched where the processor 50C use of object's clock 56B is synchronized with the processor 50B and common clock 56. Alternatively, and/or additionally, the timestamp may use a phase and period detection technique by using recent historical timestamps to determine the frequency of the electromagnetic field and use regression analysis to predict future time stamps. The predicted frequency may be audited occasionally to ensure the time has not drifted. It the frequency and accompanying timestamp has drifted, regression analysis can determine a more current timestamp for the frequency. This process can be repeated to reduce compute cycles that would otherwise be used to determine the timestamp with the location data set for each time interval.

Figure 6:
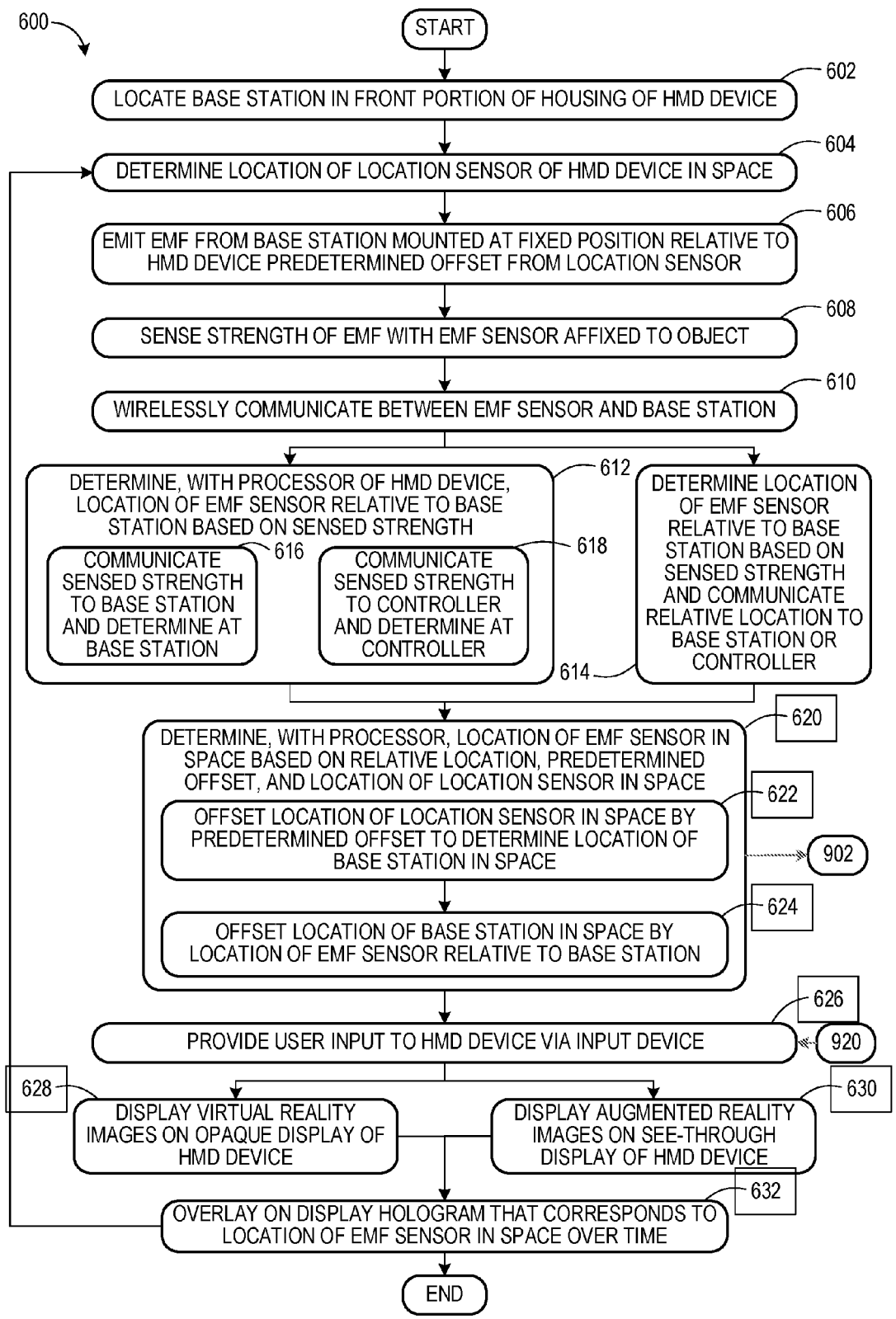
FIG. 6 shows a flowchart for a method of locating an object in the mixed reality system.

FIG. 6 shows a flowchart for a method 600 of locating an object in a mixed reality system. The following description of method 600 is provided with reference to the mixed reality system 100 described above and shown in FIG. 6. It will be appreciated that method 600 may also be performed in other contexts using other suitable components.

With reference to FIG. 6, at 602, the method 600 may include positioning a base station in a front portion of a housing of a head-mounted display (HMD) device. When the object to be located is located in front of a user wearing the HMD device, which is likely when the user is looking at or holding the object in her hands, positioning the base station in the front portion of the housing may increase accuracy, decrease noise filtering performed to calculate accurate values, and allow for a decrease in the range of the base station without negatively impacting performance. At 604, the method 600 may include determining a location of a location sensor of the HMD device in space. As mentioned above, the location sensor may include an accelerometer, a gyroscope, a global positioning system, a multilateration tracker, or one or more optical sensors such as a camera, among others. Depending on the type of sensor, the location sensor itself may be configured to determine the location, or the controller may be configured to calculate the location of the location sensor based on data received therefrom. In some instances, the location of the location sensor may be considered the location of the HMD device itself.

At 606, the method 600 may include emitting an electromagnetic field from the base station mounted at a fixed position relative to the HMD device a predetermined offset from the location sensor. The base station may be rigidly mounted near the location sensor to minimize movement between the sensors, and a precise value of the predetermined offset may be determined when calibrating the HMD device as discussed above. At 608, the method 600 may include sensing a strength of the electromagnetic field with an electromagnetic field sensor affixed to the object. The object may be an inert physical object, a living organism, or a handheld input device, for example.

At 610, the electromagnetic field sensor may comprise a transceiver and the method 600 may include wirelessly communicating between the electromagnetic field sensor and the base station. Alternatively, any of the base station, the electromagnetic field sensor, and a controller of the HMD device may be connected via a wired connection. At 612, the method 600 may include determining, with a processor of the HMD device, a location of the electromagnetic field sensor relative to the base station based on the sensed strength. Alternatively, at 614, the method 600 may include, at a processor of the electromagnetic field sensor, determining the location of the electromagnetic field sensor relative to the base station based on the sensed strength and then communicating the relative location to the base station or controller. In such a case, the processor of the HMD device, which may be of the base station or of the controller, may be considered to determine the relative location by receiving the relative location from the electromagnetic field sensor. If calculation is performed at a processor of the HMD device to determine the relative location at 612, then at 616, the method 600 may include communicating the sensed strength to the base station and determining, at the base station, the location of the electromagnetic field sensor relative to the base station based on the sensed strength. Similarly, at 618, the method 600 may include communicating the sensed strength to the controller and determining, at the controller, the location of the electromagnetic field sensor relative to the base station based on the sensed strength. Various determination processing may be distributed in a suitable manner among the various processors of the mixed reality system to lower the amount of raw data transmitted or lower the power of the processors included, for example.

At 620, the method 600 may include determining, with the processor, a location of the electromagnetic field sensor in space based on the relative location, the predetermined offset, and the location of the location sensor in space. In one example, determining the location of the electromagnetic field sensor in space at 620 may include, at 622, offsetting the location of the location sensor in space by the predetermined offset to determine a location of the base station in space, and at 624, offsetting the location of the base station in space by the location of the electromagnetic field sensor relative to the base station. As mentioned above, it will be appreciated that the "location" may include both position and orientation for a total of six values per location, and thus the offset may also include three dimensions of position and three dimensions of orientation. Further, for each of steps 620-624, the processor may be the processor of the base station or of the controller of the HMD device, or even of the electromagnetic field sensor in some cases. After determining the location of the electromagnetic field sensor in space at 620, the method may proceed to a method 900, discussed below with reference to FIG. 9, where the magnetic tracking system may be augmented to increase accuracy. The method 900 may eventually return to the method 600 at 626 so that the method 600 may be completed.

At 626, when the object is a handheld input device, the method 600 may include providing user input to the HMD device via the input device. In such a situation, the handheld input device may be used for six degree of freedom input. At 628, the method 600 may include displaying virtual reality images on an at least partially opaque display of the HMD device. At 630, the method 600 may include displaying augmented reality images on an at least partially see-through display of the HMD device. Whether opaque or see-through, the display may be controlled by the controller of the HMD device. As discussed above, the display may be configured to switch between opaque and see-through modes, or vary by degrees therebetween. Whether operating in an augmented reality mode or a virtual reality mode, at 632, the method 600 may include overlaying on the display a hologram that corresponds to the location of the electromagnetic field sensor in space over time. In order to constantly display the hologram at an updated location over time, the method 600 may return to 604 and repeat any of the steps there between. As the location of the electromagnetic field sensor changes, the controller may render images on the display to move the hologram in a corresponding manner, whether the hologram is directly overlaid on the location, is a fixed distance away from the location, or is a changing distance away from the location. In such a manner, the hologram may be seemingly seamlessly integrated with the real-world environment to the user.

Figure 7:
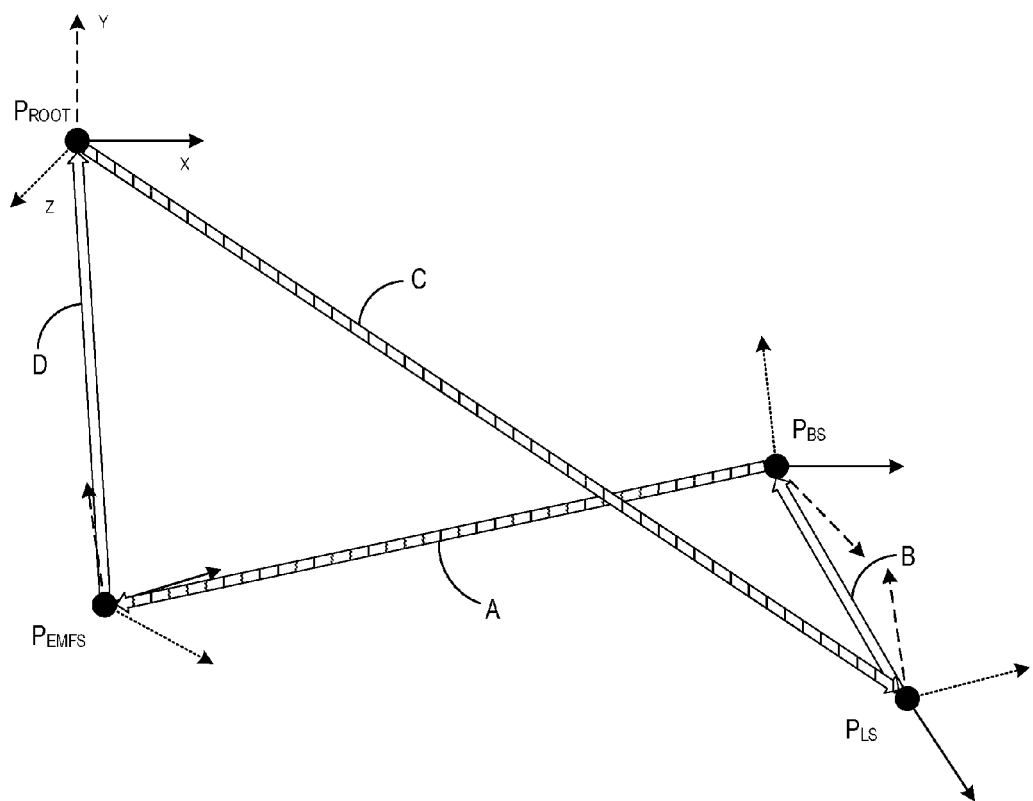
FIG. 7 shows an example calibration configuration for the mixed reality system.

FIG. 7 shows an example calibration configuration for the mixed reality system 100. During calibration, the electromagnetic field sensor 40 may be kept at a fixed position in the real world, denoted as $P_{EMFS}$. Measurements may be taken at precisely coordinated times by both the electromagnetic field sensor 40 and the location sensor 30 as the HMD device 10 is moved along a motion path that includes combined rotation and translation to cause changes in each value measured (X, Y, Z, pitch, roll, yaw) by the location sensor 30 to account for the effect that motion has on each value measured by the electromagnetic field sensor 40. Thus, the calibration may be performed by a robot in a factory where full six degree of freedom control can be ensured. In FIG. 7, like axes are shown with like lines to indicate varying orientations.

As the HMD device 10 is moved along the motion path, the measurements taken over time may include data relating to the location of the location sensor 30 ($P_{LS}$), the location of the base station 36 ($P_{BS}$), the location of the electromagnetic field sensor 40 ($P_{EMFS}$), and the location of an arbitrary fixed point in the real world relative to which the HMD device 10 reports its location ($P_{ROOT}$). This fixed point $P_{ROOT}$ may be, for example, the location of the HMD device 10 when it is turned on or a current software application starts, and the fixed point may be kept constant throughout an entire use session of the HMD device 10. The HMD device 10 may be considered to "tare" or "zero" its position in space by setting the fixed point $P_{ROOT}$ as the origin (0,0,0,0,0,0) and reporting the current location of the location sensor as coordinates relative thereto.

The measurements taken during calibration may include a matrix or transform A representing the temporarily-fixed real-world point $P_{EMFS}$ relative to the moving location $P_{BS}$, and a matrix or transform C representing the moving location $P_{LS}$ relative to the fixed real-world point $P_{ROOT}$. The matrix A may correspond to measurements taken by the electromagnetic field sensor 40 and the matrix C may correspond to measurements taken by the location sensor 30. In FIG. 7, transforms which are measured are shown as striped arrows, while previously unknown transforms to be calculated during calculation are shown as white arrows. The transforms A, B, C, and D form a closed loop in FIG. 7. Therefore, once sufficient data has been collected, an optimization algorithm may be performed to converge on a single solution for the matrices or transforms B and D in Equation 1 below, where I is an identity matrix of an appropriate size.

$$A \times B \times C \times D = I \qquad \text{Equation 1:}$$

Solving for the matrix B may provide the predetermined offset 60, which may be six values including three dimensions of position and three dimensions of orientation, which may then be used during normal operation to align measurements of the electromagnetic field sensor 40 and the location sensor 30 to the same reference point. Thus, during normal operation of the HMD device 10, in order to determine the location 58 of the electromagnetic field sensor 40 in space, the processor 50A, 50B, or 50C may be configured to offset the location 62 of the location sensor 30 in space by the predetermined offset 60 to determine the location of the base station 36 in space. Then, the processor 50A, 50B, or 50C may be configured to offset the location of the base station 36 in space by the relative location 18 of the electromagnetic field sensor 40 relative to the base station 36.

B) Capture Pose Data from an Optical Tracking System

Figure 8:
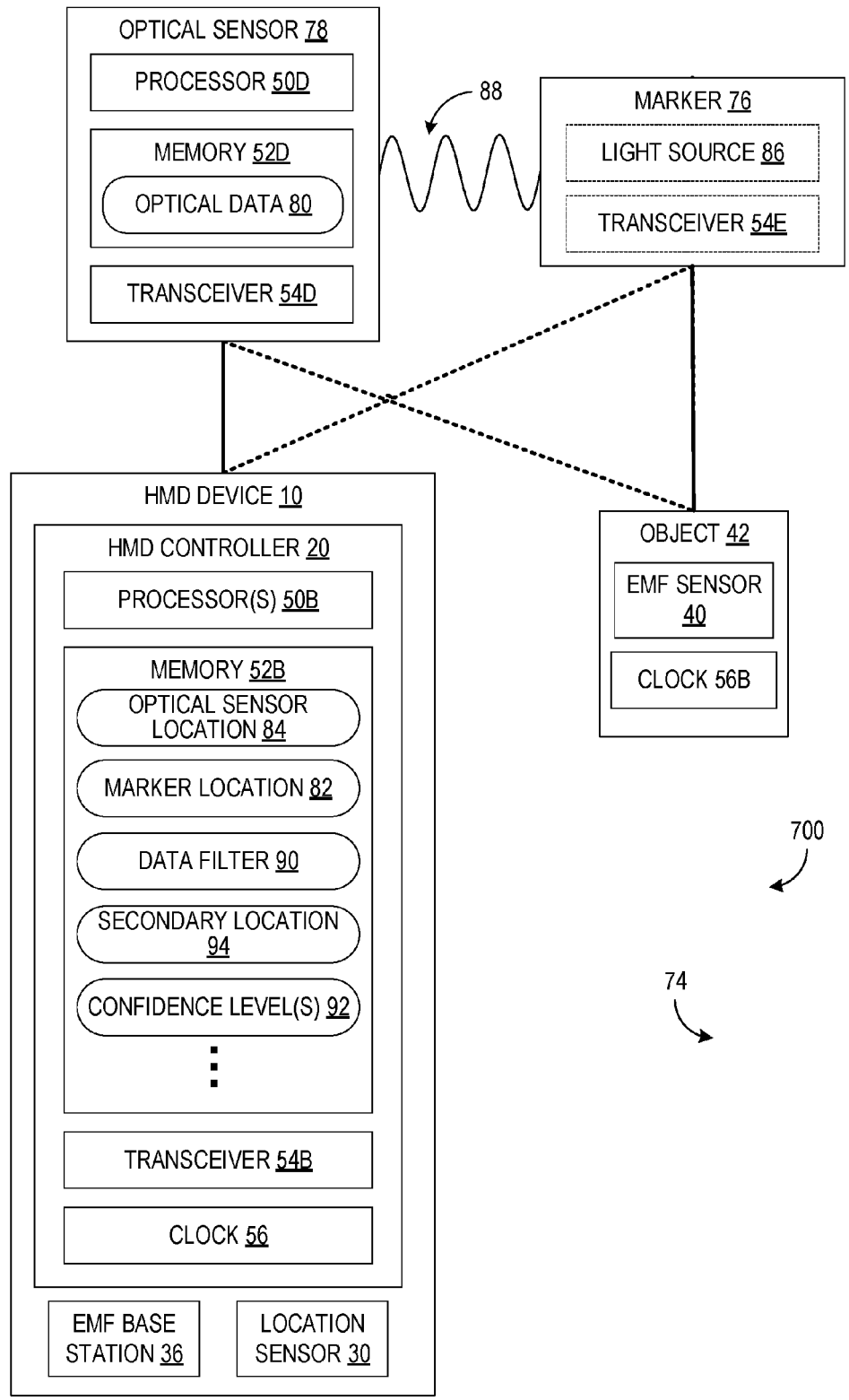
FIG. 8 shows an example software-hardware diagram of a mixed reality system including an optical tracking system.

Referring again to FIG. 1, the HMD device 10 may include an optical tracking system to track a real world object and capture data corresponding to the pose of the real world object (act 120). FIG. 8 shows an example software-hardware diagram of a mixed reality system 700 including an optical tracking system. The mixed reality system 700 may include some or all components of the nixed reality system 100 of FIG. 5, and may additionally comprise an optical tracking system 74 comprising at least one marker 76 and at least one optical sensor 78 configured to capture optical data 80. Description of identical components and processes performed thereby will not be repeated, for brevity.

The optical sensor 78 may comprise a processor 50D, memory 52D, and transceiver 54D, or may utilize any of the processors 50A-C, memory 52A-C, and transceiver 54A-C as suitable. The optical data 80 captured by the optical sensor 78 may be stored in the memory 52D. The optical data 80 may be used by the processor 50D to determine a location 82 of the marker 76 and/or a location 84 of the optical sensor 78 that is transmitted to the controller 20, or the optical data 80 itself may be transmitted to the controller 20 so that the processor 50B may determine the locations 82, 84. The optical sensor 78 may be, for example, an image sensor such as an infrared camera, color camera, or depth camera, or a lidar device. The HMD device 10 is shown in FIG. 2 having a separate optical sensor 78 that may be an infrared camera, but it may instead utilize one of the sensors of the position sensor system 28, including the location sensor 30, if a suitable optical sensor is included. When the optical sensor 78 is a type of camera, the location 82 of the marker 76 may be determined through computer vision or image processing of an image or video captured by the optical sensor 78 of the marker 76. The location 82 of the marker 76 may be a relative location compared to the optical sensor 78 or a location in space. A relative location may be converted into a location in space by translating the location 82 based on a known location 84 of the optical sensor 78.

As shown in solid lines, the optical tracking system 74 may be configured with the at least one optical sensor 78 on the HMD device 10 and the at least one marker 76 on the object 42. In this case, the optical sensor 78, similar to the base station 36, may be located a fixed offset away from the location sensor 30, and the location 82 of the marker 76 can easily be determined based on the optical data 80, the location 84 of the optical sensor 78, and the fixed offset. Alternatively, as shown in dotted lines, the optical tracking system 74 may be configured with the at least one optical sensor 78 on the object 42 and the at least one marker 76 on the HMD device 10. In this case, the location 82 of the marker 76 may be a fixed offset away from the location sensor 30 on the HMD device 10, and the location 84 of the optical sensor 78 may be determined based on the optical data 80, the location 82 of the marker 76, and the fixed offset. In either case, the location of the portion of the optical tracking system 74 on the object 42 may be determined. FIG. 2 shows either the optical sensor 78 or the marker(s) 76, drawn in dashed lines, being included in the HMD device 10.

The marker 76 may comprise a light source 86 configured to actively emit light 88, referred to herein as an active marker. The light 88 may be of a corresponding type to be detected by the optical sensor 78, for example, infrared light with an infrared camera, visible light with a color camera, etc. With the light source 86, the active marker 76 may be controlled to emit only at certain times, in a specified pattern, at a specified brightness, or in a specified color, etc. This may decrease failed or mistaken recognition of the marker 76 and increase the accuracy of the optical tracking system 74. In this case, the marker 76 may include a transceiver 54E to communicate with a processor in control of operating the light source 86, or the marker 76 may be wired thereto directly. Alternatively, the marker 76 may be reflective, referred to herein as a passive marker. The passive marker 76 may reflect the light 88 due to inclusion of a reflective film, or retro-reflective tape or paint in its construction, for example. If the optical tracking system 74 is able to accurately track the location 82 of the passive marker 76, then the mixed reality system 700 may experience lower energy usage as compared to a situation in which an active marker 76 is used. In addition, the transceiver 54E may be omitted from the marker 76 when the marker 76 is reflective, lowering the power and processing burden of the HMD device 10 or object 42.

When the optical sensor 78 is a type of camera, the camera may capture images at a predefined rate, for example 60 frames per second (FPS). The location 82 of the marker 76 may be determined through computer vision or image processing of an image or video captured by the optical sensor 78 of the marker 76. In addition, the pose of the object may be determined through computer vision or image processing. In one embodiment, the image capture rate of 60 FPS creates an image every 16.67 milliseconds. The predefined frame rate may support an image capture rate substantially faster or slower than 60 FPS.

Figure 9:
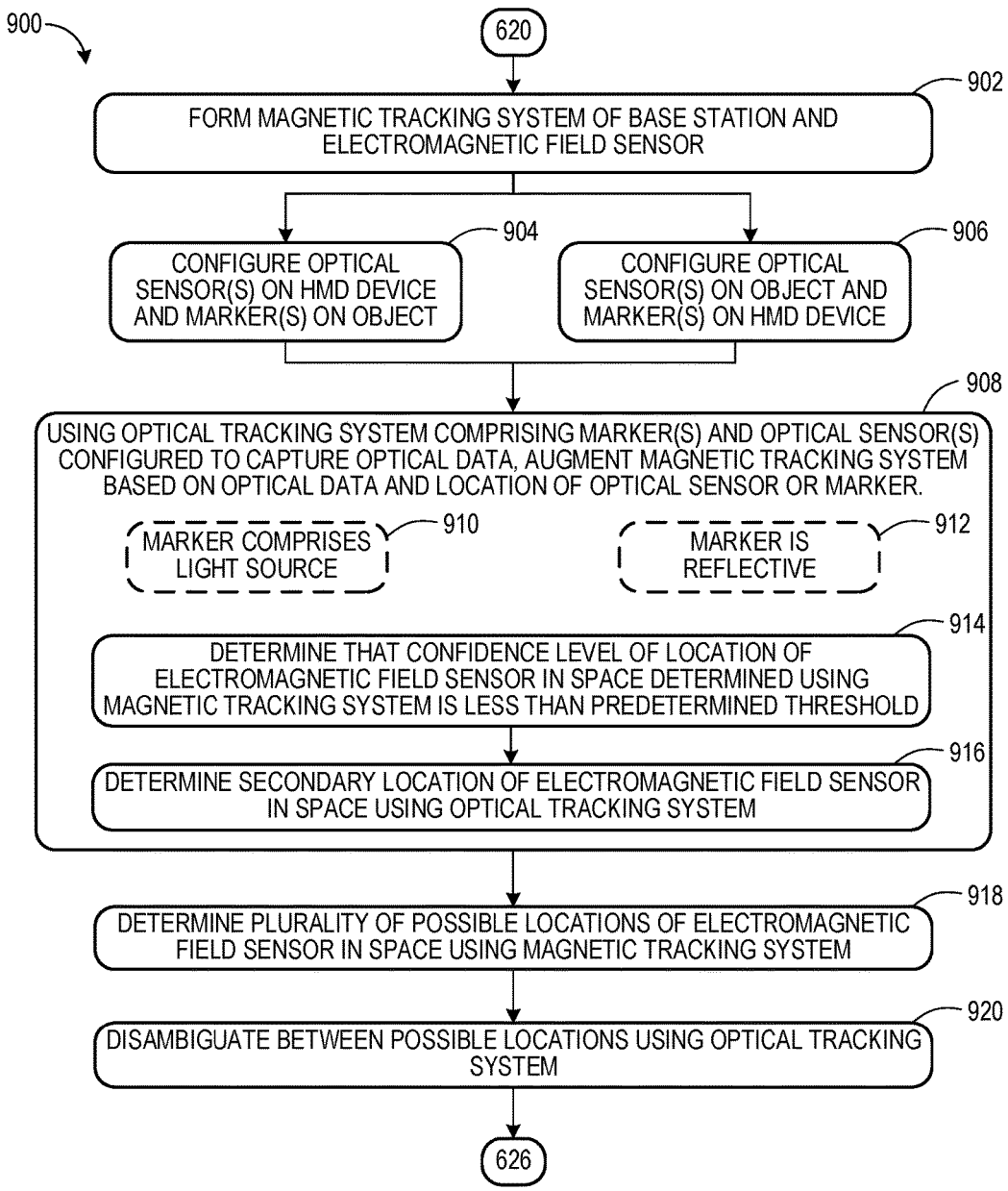
FIG. 9 shows a flowchart for a method of augmenting the method of FIG. 6.

FIG. 9 shows a flowchart for a method 900 of locating an object in a mixed reality system. The method 900 may continue from the method 600 and may return to the method 600 upon completion. The following description of method 900 is provided with reference to the mixed reality system 100 described above and shown in FIG. 7. It will be appreciated that method 900 may also be performed in other contexts using other suitable components.

As discussed above, the method 600 may include determining, with the processor, the location of the electromagnetic field sensor in space based on the relative location, the predetermined offset, and the location of the location sensor in space at 620. At 902, the base station and electromagnetic field sensor together may form a magnetic tracking system. At 904, the method 900 may include configuring at least one optical sensor on the HMD device and at least one marker on the object; alternatively, at 906, the method 900 may include configuring the at least one optical sensor on the object and the at least one marker on the HMD device. In one example, the optical sensor may be placed on the component that has other uses for the optical sensor beyond locating the object to avoid adding a single-purpose sensor, and the marker may be placed on the component with the lower power capacity to lower power consumption.

At 908, the method 900 may include using an optical tracking system comprising the at least one marker and the at least one optical sensor configured to capture optical data, augmenting the magnetic tracking system based on the optical data and a location of the optical sensor or marker. In doing so, at 910, the marker may comprise a light source; alternatively, at 912, the marker may be reflective. A light source may emit a brighter, focused light compared to a reflective marker, thereby increasing detection accuracy, but may also use more power. Further, at 914, augmenting the magnetic tracking system may comprise determining that a confidence level of the location of the electromagnetic field sensor in space determined using the magnetic tracking system is less than a predetermined threshold, and at 916, determining a secondary location of the electromagnetic field sensor in space using the optical tracking system. As discussed above, the magnetic tracking system may become unreliable and data from the optical tracking system may be prioritized when the threshold is not met.

As discussed previously, at 626, the object may be a handheld input device configured to provide user input to the HMD device. With the optical tracking system included, the handheld input device may comprise a housing including a grip area and the at least one marker or the at least one optical sensor may be located on at least one protuberance that extends outside of the grip area. In such a manner, the marker(s) and optical sensor(s) may be able to communicate reliably without interference from the user's hand.

At 918, the method 900 may include determining a plurality of possible locations of the electromagnetic field sensor in space using the magnetic tracking system. The plurality of possible locations may include one true location and one or more false locations. At 920, the method 900 may include disambiguating between the possible locations using the optical tracking system. As discussed above, this may include assuming that the current location is most likely to be near an immediately previously determined location rather than one of the other possible locations that is farther away. After 920, the method 900 may return to the method 600 at 626, although it will be appreciated that the methods 600 and 900 may be combined in other suitable manners.

The above mixed reality systems and methods of locating an object therein may utilize a magnetic tracking system consisting of a paired electromagnetic base station and sensor to track the object affixed to the sensor, and an optical tracking system consisting of a paired optical sensor and marker to augment the magnetic tracking system. The optical tracking system may serve to provide points of reference to disambiguate between multiple locations calculated by the magnetic tracking system, or data from both systems may be weighted dynamically as each system becomes more or less reliable due to changing circumstances. The mixed reality system thus may intelligently reduce power in unreliable systems and quickly respond to the changing position of the object when rendering graphics tethered to the object, increasing the quality of the user experience.

In some embodiments, the methods and processes described herein may be tied to a computing system of one or more computing devices. In particular, such methods and processes may be implemented as a computer-application program or service, an application-programming interface (API), a library, and/or other computer-program product.

C) Capture Pose Data from an Alternative Tracking System

Referring again to FIG. 1, the HMD device 10 may include one or more alternative tracking system to track a real world object and capture data corresponding to the pose of the real world object (act 130). For example, the alternative tracking systems may be an inertial measurement unit (IMU), an optical sensor, and/or a time of flight camera.

Figure 10A:
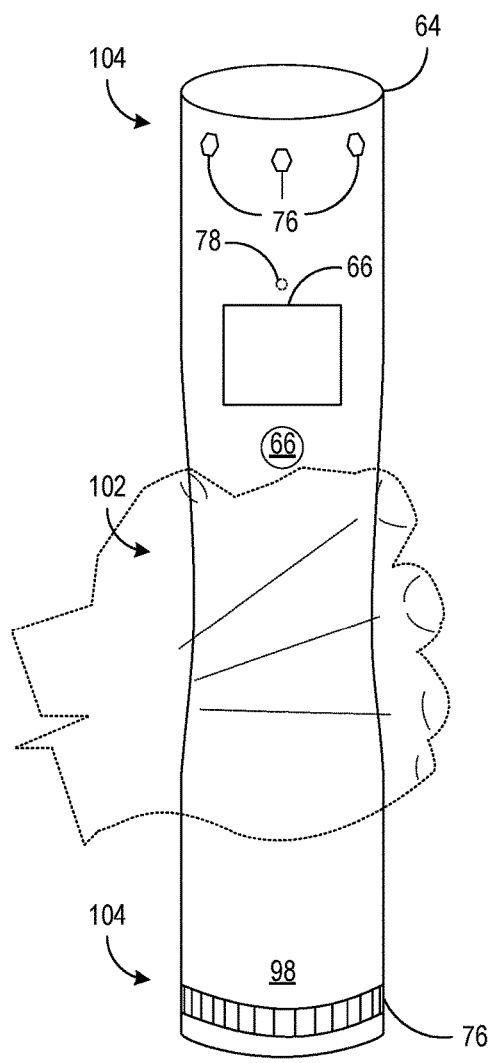
FIGS. 10A and 10B respectively show front and back views of an example handheld input device of the mixed reality system.
Figure 10B:
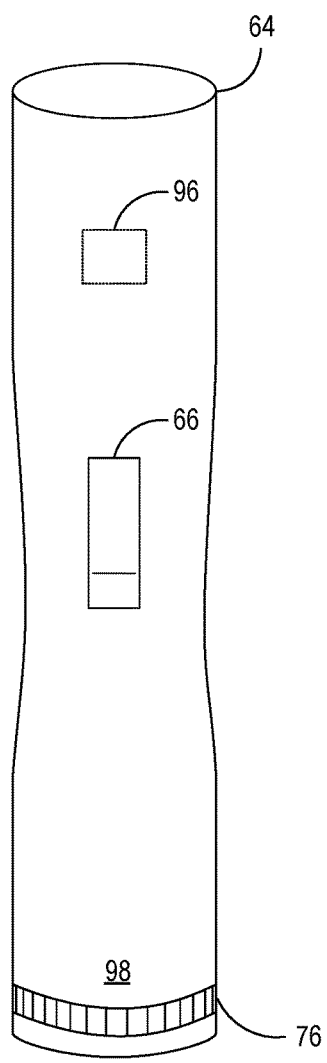

FIGS. 10A and 10B respectively show front and back views of an example handheld input device 64 of the mixed reality system 700. As discussed above, the object 42 may be a handheld input device 64 configured to provide user input to the HMD device 10. FIGS. 10A and 10B show several examples of the input controls 66 mentioned above. A touch screen and button are shown in FIG. 8 while a trigger is shown in FIG. 10B. The handheld input device 64 also may include the IMU 96 mentioned above, which itself may be used as an input controls 66 responsive to movement in three dimensions and rotation in three dimensions for a total of six degrees of freedom. The IMU 96 may comprise a sensor suite including a gyroscope and accelerometer, and optionally a magnetometer. The IMU 96 may be configured to measure a change in acceleration with the accelerometer and a change in orientation (pitch, roll, and yaw) with the gyroscope, and may use data from the magnetometer to adjust for drift.

In this example, the handheld input device 64 may comprise a housing 98 including a grip area 102 and the at least one marker 76 or the at least one optical sensor 78 may be located on at least one protuberance 104 that extends outside of the grip area 102. The marker(s) may be located on only one protuberance 104 or on two or more if more are present. Locating the marker(s) 76 on the protuberance 104 may reduce instances of occlusion of the marker(s) by the user's hand, which is generally located in the grip area 102. The example in FIG. 10A shows multiple markers 76. Some markers 76, such as those on the top protuberance 104, are placed intermittently around the circumference of the protuberance 104 and do not extend fully around to the back side of the handheld input device 64, as shown in FIG. 10B. The markers 76 on the bottom protuberance 104 are examples of markers that extend fully around the circumference of the protuberance 104. The upper markers 76 may each comprise a light source such as a light-emitting diode (LED), while the lower markers 76 may be reflective. Alternatively, the markers 76 may be located on the HMD device 10 and the optical sensor 78 may be located on the handheld input device 64, as shown in dashed lines.

D) Alternative Embodiments for Tracking Systems

Figure 11:
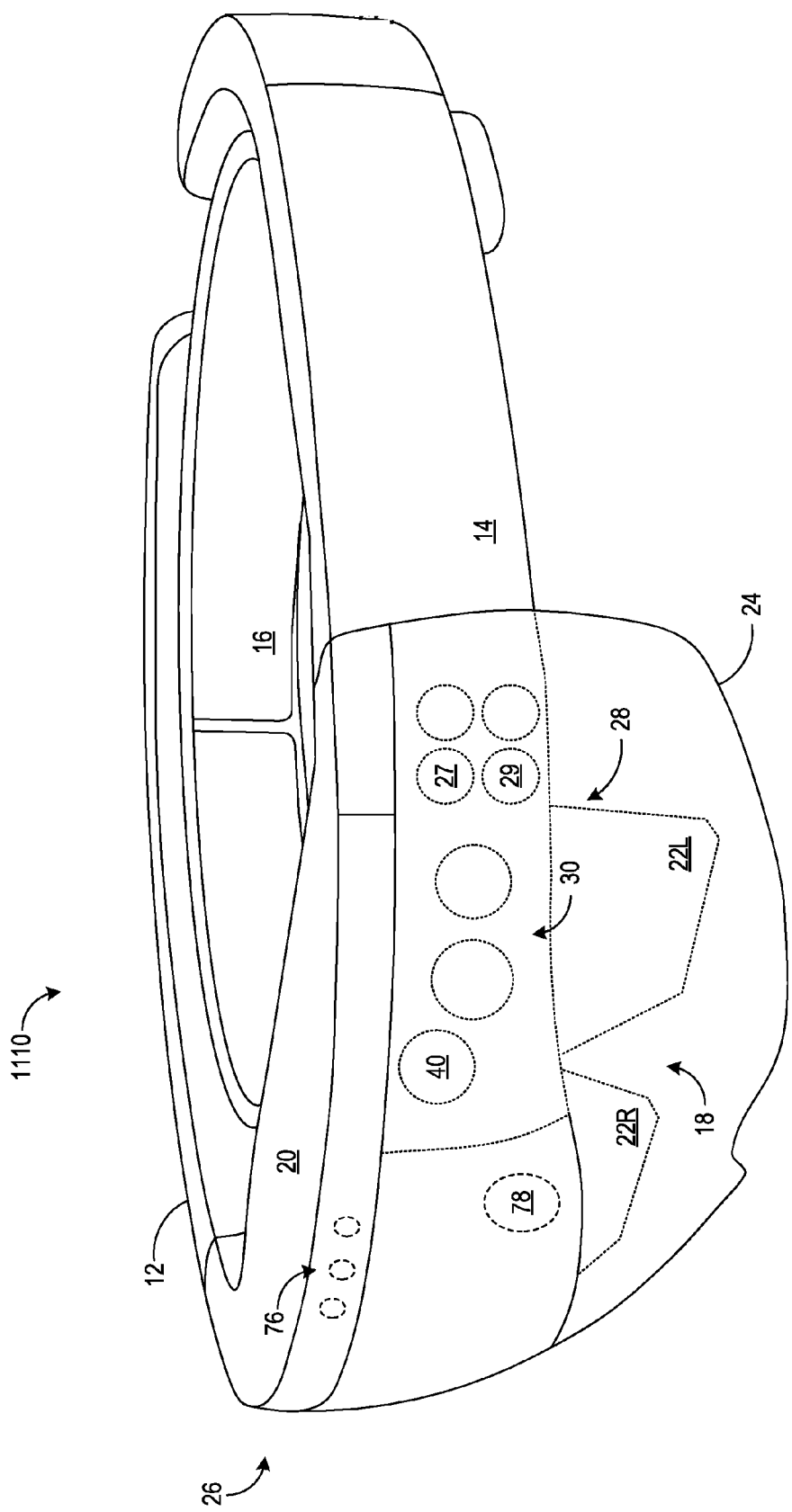
FIG. 11 shows a schematic illustration of an HMD device according to an alternative configuration.
Figure 12:
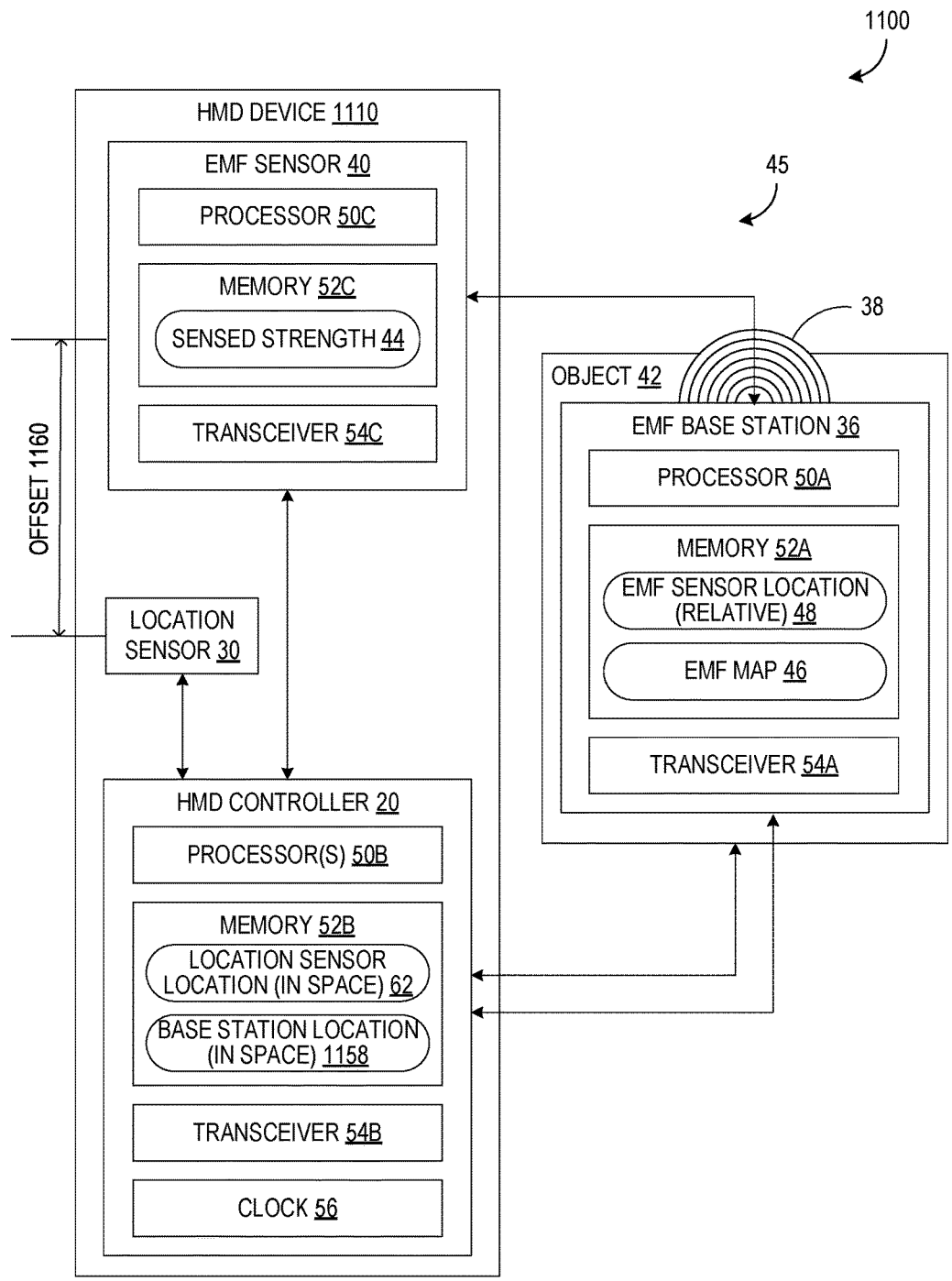
FIG. 12 shows an example software-hardware diagram of a mixed reality system including the HMD device according to the alternative configuration.

Embodiments described above may include alternative embodiments. The above description is of a mixed reality system 100 of a first configuration in which the HMD device 10 comprises the base station 36 and the electromagnetic field sensor 40 is affixed to the object 42. However, FIG. 11 shows a schematic illustration of an HMD device 1110 according to an alternative configuration, and FIG. 12 shows an example software-hardware diagram of a mixed reality system 1100 including the HMD device 1110 according to the alternative configuration. In the alternative configuration, many components are substantially the same as in the first configuration and therefore description thereof will not be repeated. According to the alternative configuration, the mixed reality system 1100 may comprise the base station 36 affixed to the object 42 and configured to emit the electromagnetic field 38, and the HMD device 1110 may comprise the electromagnetic field sensor 40 mounted at a fixed position relative to the HMD device 1110 a predetermined offset 1160 from the location sensor 30 and configured to sense the strength 44 of the electromagnetic field 38. After the relative location 48 of the electromagnetic field sensor 40 is determined as discussed above, the processor 50A, 50B, or 50C may be configured to determine a location 1158 of the base station 36 in space based on the relative location 48, the predetermined offset 1160, and the location 62 of the location sensor 30 in space.

Figure 13:
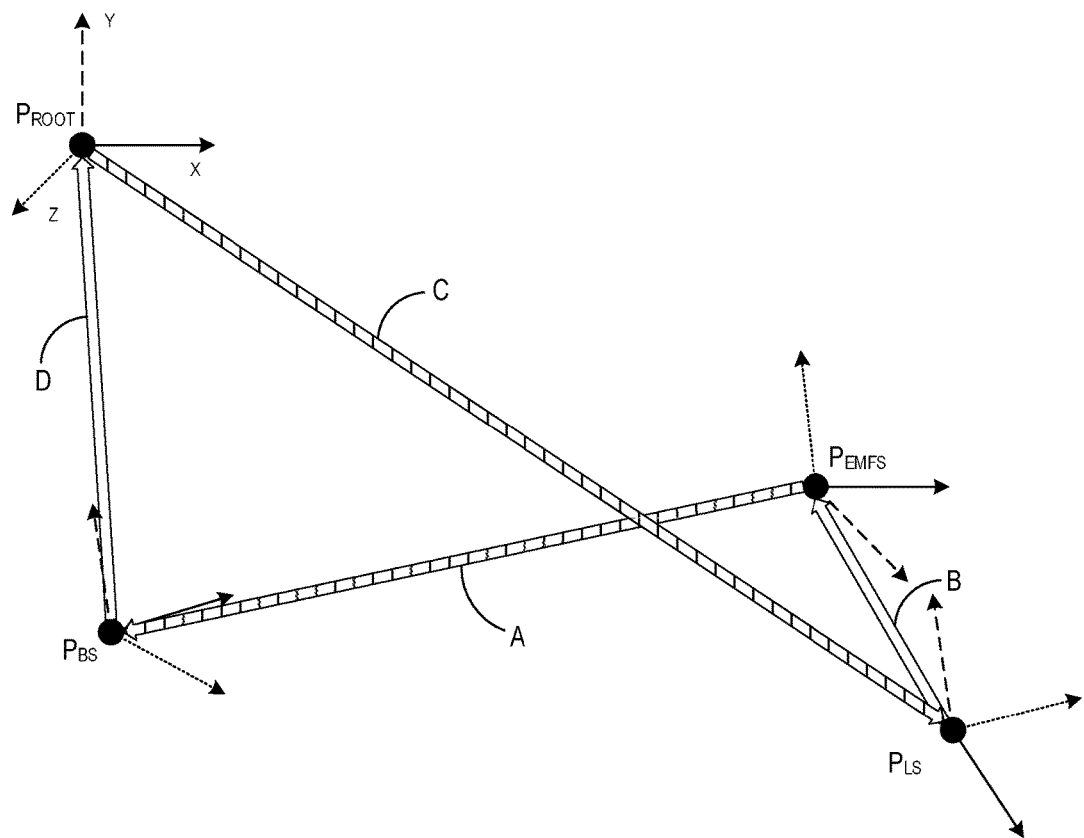
FIG. 13 shows an example calibration configuration for the mixed reality system according to the alternative configuration.

FIG. 13 shows an example calibration configuration for the mixed reality system 1100 according to the alternative configuration. Calibration is similar to the calibration for the first configuration, except that $P_{BS}$ and $P_{EMFS}$ are switched. To account for the matrix A transforming from $P_{EMFS}$ to $P_{BS}$, the sensed strength may be used to determine the location of the base station 36 relative to the electromagnetic field sensor 40, inverted from the relative location 48.

Figure 14:
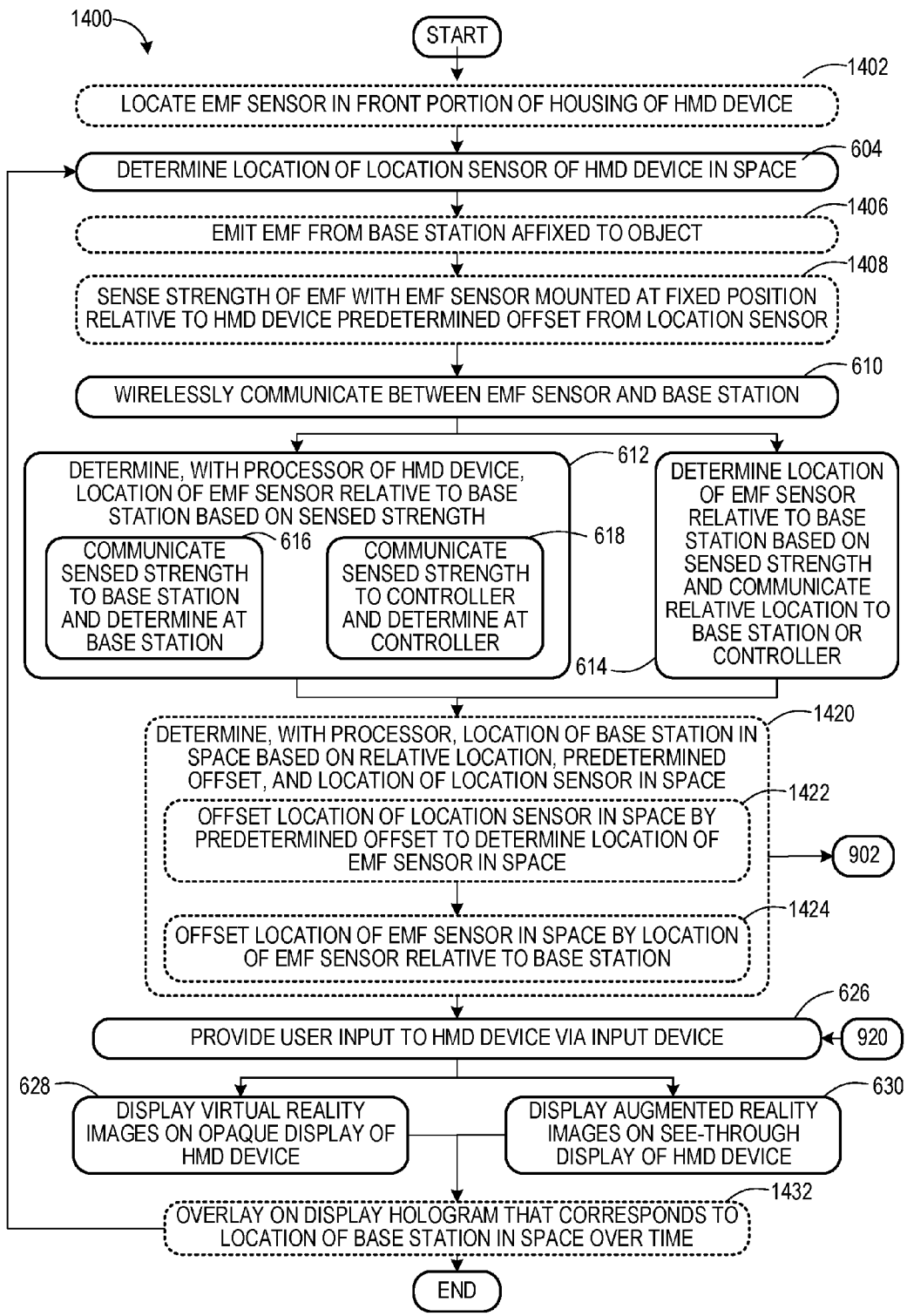
FIG. 14 shows a flowchart for a method of locating an object in the mixed reality system according to the alternative configuration.

FIG. 14 shows a flowchart for a method 1400 of locating an object in the mixed reality system according to the alternative configuration. The steps of method 1400 correspond to the steps of method 600 except where shown in dotted lines in FIG. 14, and description of duplicate steps will not be repeated.

With reference to FIG. 14, at 1402, the method 1400 may include locating an electromagnetic field sensor in a front portion of a housing of an HMD device. At 1406, the method 1400 may include emitting an electromagnetic field from a base station affixed to the object. At 1408, the method 1400 may include sensing a strength of the electromagnetic field with an electromagnetic field sensor mounted at a fixed position relative to the HMD device a predetermined offset from the location sensor. At 1420, the method 1400 may include determining, with a processor of the HMD device, a location of the electromagnetic field sensor relative to the base station based on the sensed strength. In one example, determining the location of the base station in space at 1420 may include, at 1422, offsetting the location of the location sensor in space by the predetermined offset to determine the location of the electromagnetic field sensor in space, and at 1424, offsetting the location of the electromagnetic field sensor in space by the location of the electromagnetic field sensor relative to the base station. Finally, at 1432, the method 1400 may include overlaying on a display a hologram that corresponds to the location of the base station in space over time.

Figure 15:
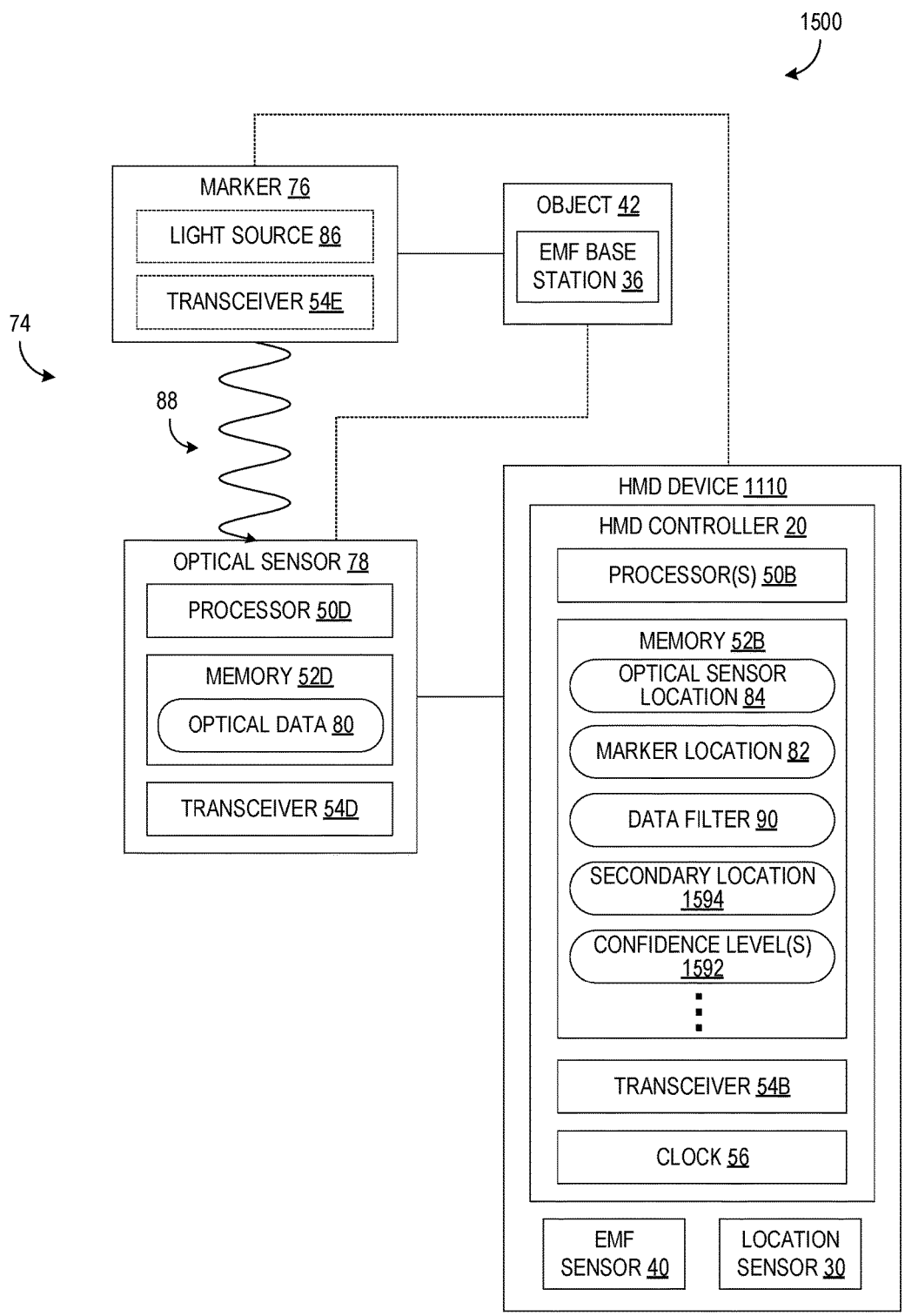
FIG. 15 shows an example software-hardware diagram of a mixed reality system including an optical tracking system according to the alternative configuration.

FIG. 15 shows an example software-hardware diagram of a mixed reality system 1500 including the optical tracking system 74 according to the alternative configuration. Similarly to the first configuration above, the processor 50A, 50B, or 50C may be configured to determine a plurality of possible locations of the base station 36 in space using the magnetic tracking system 45 and disambiguate between the possible locations using the optical tracking system 74. In one example, in order to augment the magnetic tracking system 45, the processor 50A, 50B, or 50C is configured to determine that a confidence level 1592 of the location 1158 of the base station 36 in space determined using the magnetic tracking system 45 is less than the predetermined threshold. The confidence level may be based at least on a change in the location 1158 of the base station 36 in space over time. Then, the processor 50A, 50B, and 50C may be configured to determine a secondary location 1591 of the base station 36 in space using the optical tracking system 74.

Figure 16:
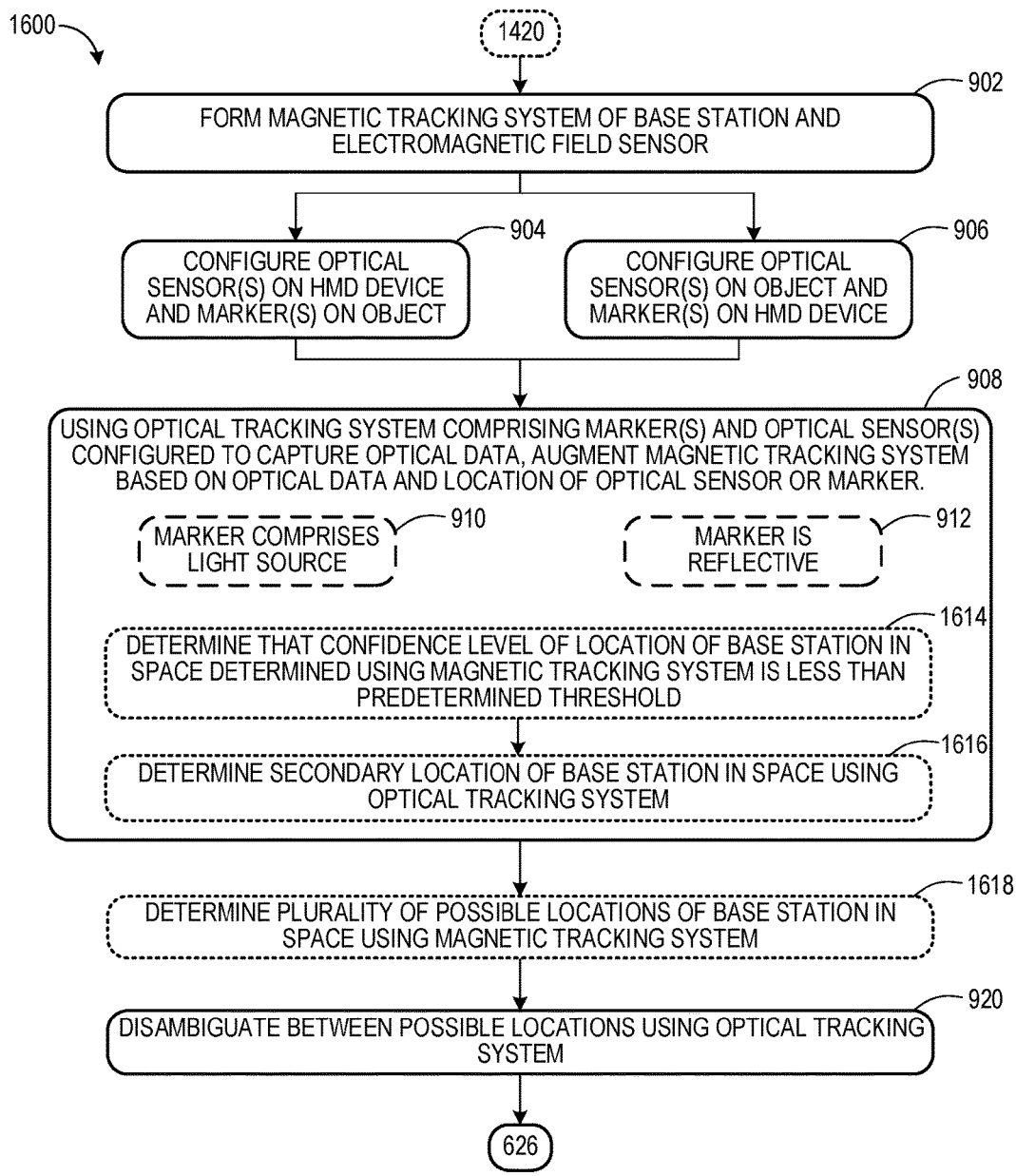
FIG. 16 shows a flowchart for a method of augmenting the method of FIG. 14.

FIG. 16 shows a flowchart for a method 1600 of augmenting the method 1400 of FIG. 14. The steps of method 1600 correspond to the steps of method 900 except where shown in dotted lines in FIG. 16, and description of duplicate steps will not be repeated.

As discussed above, the method 1400 may include determining, with a processor of the HMD device, a location of the electromagnetic field sensor relative to the base station based on the sensed strength at 1420. The method 1600 may begin thereafter, at 902, or at another suitable point. At 1614, the method 900 may include determining that a confidence level of the location of the base station in space determined using the magnetic tracking system is less than a predetermined threshold. At 1616, the method 1600 may include determining a secondary location of the base station in space using the optical tracking system. Further, at 1618, the method 1600 may include determining a plurality of possible locations of the base station in space using the magnetic tracking system.

Although the configurations described above include one HMD device 10, 1110 and one object 42, more than one may be included in the mixed reality system. For example, a user may wear the HMD device 10, 1110 and hold one handheld input device 64 as the object 42 in each hand. In such a situation, the HMD device 10, 1110 may be configured to overlay respective holograms 33 on the display 18 that independently track each handheld input device 64. The magnetic tracking system 45 may be configured with the base station 36 on one handheld input device 64, one electromagnetic field sensor 40 on the other handheld input device 64, and an additional electromagnetic field sensor 40 on the HMD device 1110. The HMD device 10 may instead include the base station 36, but placing it on one of the handheld input devices 64 frees up space and uses less power on the HMD device 1110. The HMD device 1110 may determine the locations of each handheld input device 64 or portions of the calculations in making the determinations may be distributed among various processors in the mixed reality system as discussed above. Furthermore, the number of handheld input devices 64 is not limited to two and may be any suitable number. The handheld input devices 64 may be operated by multiple users as well.

In one alternative example, each handheld input device 64 may comprise its own base station 36 configured to emit an electromagnetic field 38 at a respective frequency, thereby avoiding interference with each other. The HMD device 1110 then comprises an electromagnetic field sensor 40 to complete the magnetic tracking system 45. These multi-object systems are not limited to handheld input devices 64 and may instead include other types of objects 42. Further, as with the single-object mixed reality systems discussed above, the multi-object systems may also comprise the optical tracking system 74 which may be distributed in any suitable manner. For example, the HMD device 10, 1110 may comprise the optical sensor 78 and each handheld input device 64 may comprise the optical marker(s) 76, the HMD device 10, 1110 may comprise the optical marker(s) 76 and each handheld input device 64 may comprise the optical sensor 78, or the HMD device 10, 1110 and one handheld input device 64 may comprise the optical sensor 78 while the other handheld input device 64 comprises the optical marker(s) 76. Using both tracking systems together in a multi-object system may increase accuracy by disambiguating between magnetic or optical input from multiple sources.

F) Fuse Data from Multiple Tracking Systems

Referring again to FIG. 1, the data acquired by two or more tracking systems may be used to create a homogenous tracking model of the real-world object (act 140). In one embodiment, a homogenous data set for tracking the real-world object may fuse together data from the optical tracking system 74 and the magnetic tracking system 45. Here, the processor 50B may be configured to determine the pose of the object 42 from an image captured by the optical sensor 78. The pose of the object and the location 84, 82 of the optical sensor 78 or marker 76 may be determined through computer vision or image processing of an image captured optical sensor 78. For example, an optical sensor 78 may capture images at a predefined rate of sixty frames per second (FPS), or an image every 16.667 milliseconds. However, the pose of a handheld object may change significantly in a 16.667 millisecond period. As such, the pose of the object may be tracked at a more frequent rate by another tracking system. For example, the relative change in pose may be tracked by the magnetic tracking system 45 until the processor 50B has a subsequent image to determine the pose of object 42. As an example, the magnetic tracking system 45 may track the object 42 with an EMF signal 38 of 250 kHz. At this electromagnetic frequency, for each captured image the magnetic tracking system 45 may capture more than 4,000 pose data sets. This fused data set provides a pose data set that is more accurate than a single tracking system thereby enabling a more accurate model for predicting a future pose of the object 42. The predefined frame rate of the optical sensor 78 may support an image capture rate substantially faster or slower than 60 FPS. Alternatively, or additionally, processors 50A, 50C, and/or 50D may be used to fuse the pose data sets.

The processor 50B may use a data filter 90 to perform sensor fusion of the optical tracking system 74 and the magnetic tracking system 45. The data filter 90 may be, for example, a direct extrapolation, static exponential smoothing, dynamic exponential smoothing, Kalman filter, or other algorithm(s) capable of estimating confidence and weighting multiple data streams.

In order to synchronize the timing of the measurements performed by the independent tracking systems, the controller 20 may include a common clock 56 to provide timestamps for data reporting from the multiple tracking systems. An alternative embodiment may use a fixed time delay determined by known hardware and software latencies to synchronize the measurements. As an alternative embodiment, an algorithm may be used to synchronize two or more clocks. For example, processor 50B may use common clock 56 and an algorithm to synchronize the time on the processor 50C and the object's clock 56B. As an alternative example, the synchronization of clocks may be in reverse where the processor 50C use of object's clock 56B is synchronized with the processor 50B and clock 56.

As an alternative, or additional, embodiment, the processor 50B may be further configured to disambiguate the pose data from the magnetic tracking system 45. The processor 50B may be configured to determine a plurality of possible locations of the electromagnetic field sensor 40 in space using the magnetic tracking system 45 and disambiguate between the possible locations using the optical data 80 from the optical tracking system 74. An alternative embodiment may use data from the IMU 96 to disambiguate the data from the magnetic tracking system 45. For example, the IMU data may identify a clockwise rotation of the object and the data from the magnetic tracking system may have ambiguity as to the rotational direction of the object. Alternatively, the data from a second tracking system may be used to disambiguate the pose data from the magnetic tracking system. The plurality of possible locations may be determined because electromagnetic field sensors and base stations may be each formed of three orthogonal coils, one for each coordinate axis, and the magnetic tracking system 45 may tend to track within one hemisphere at a time. In some cases, the magnetic tracking system 45 may be unable to resolve the phase difference and determine which possible location is false. When tracking over time, the base station 36, or whichever specific processor is configured to determine the location 58 from the sensed strength 44, may assume that the current location is most likely to be near an immediately previously determined location rather than one in the opposite hemisphere.

However, if the object 42 is temporarily moved beyond the transmission range of the base station 36, then the magnetic tracking system 45 may not be able to disambiguate between the possible locations on its own. Thus, the optical tracking system 74 may augment the magnetic tracking system 45 by disambiguating between the possible locations and determining the most likely location. Disambiguating between the possible locations may comprise comparing the possible locations to where the location 58 of the electromagnetic field sensor 40 could be expected to likely be based on the location 84 of the optical sensor 78 or the location 82 of the marker 76, whichever component of the optical tracking system 74 is located on the object 42, and a second predetermined offset between the optical component and the electromagnetic field sensor 40. The possible location that most closely matches the expected location based on the optical tracking system 74 may be determined to be the actual location of the electromagnetic field sensor 40.

As an alternative embodiment, the magnetic tracking system 45 may be augmented by any of the secondary tracking systems included in the HMD. For example, the IMU data may be used to augment the magnetic data by disambiguating the pose data. As an alternative example, the optical sensor may provide pose or location data that may be used to augment the magnetic tracking system.

In alternative embodiment, in order to augment the magnetic tracking system 45, the processor 50B may be configured to determine that a confidence level 92 of the location 58 of the electromagnetic field sensor 40 in space determined using the magnetic tracking system 45 is less than a predetermined threshold, and determine a secondary location 94 of the electromagnetic field sensor 40 in space using the optical tracking system 74. The secondary location 94 may be estimated based on the location 82 or 84 determined by the optical tracking system 74, which may be the second predetermined offset from the electromagnetic field sensor 40. The processor 50B may be configured to execute the data filter 90 to compare the confidence level 92 to the threshold. When the confidence level 92 meets or exceeds the threshold, the processor 50B may be configured to use the location 58 from the magnetic tracking system 45 as the true location when performing further actions based on the location of the object 42, such as displaying holograms that move together with the object 42. When the confidence level 92 is less than the threshold, the processor SOB may be configured to instead use the secondary location 94 from the optical tracking system 74. In some instances, the confidence level 92 may be determined at least in part by comparing the location 58 to the secondary location 94, where a low confidence level 92 corresponds to a large difference between locations and a high confidence level 92 corresponds to a small difference between locations.

The data filter 90 may be used to determine which data stream to prioritize over the other based on the confidence level 92 of each system, which may result in lowering the power of the non-prioritized system, or even turning the system off. For example, the magnetic tracking system 45 may fail due to ambient interference or close proximity to a large piece of metal, and may be unreliable near the edge of the transmission range of the base station 36. When the confidence level 92 is determined to be below the threshold, the processor 50B may use the secondary location 94 from the optical tracking system 74, and may additionally lower the sampling rate of the electromagnetic field sensor 40 while the data from the magnetic tracking system 45 is considered unreliable. Alternatively, the base station 36 may be configured to change the frequency of the emitted electromagnetic field 38 in response to failing to meet the confidence threshold. A different frequency may reduce interference and increase accuracy of subsequent tracking by the magnetic tracking system 45. In some cases, the magnetic tracking system 45 may be a primary system, the optical tracking system 74 may be a secondary system, and the mixed reality system 700 may comprise a tertiary system such as an IMU 96, discussed below, and the processor 50B may use inertial data from the IMU 96, or other data from another tertiary system, to further supplement the determination and confirmation of the location 58.

The threshold may consist of multiple thresholds with various actions performed after each threshold is failed or met. For example, the base station 36 may change frequency after failing to meet a first threshold, the data filter 90 may prioritize the second location from the optical tracking system 74 over the location 58 from the magnetic tracking system 45 after failing to meet a second threshold, and the magnetic tracking system 45 may be temporarily turned off after failing to meet a third threshold. The confidence level 92 may be calculated based on a variety of factors. For example, the confidence level may be based at least on a change in the location 58 of the electromagnetic field sensor 40 in space over time. If the location 58 moves too quickly or erratically over time to likely be accurate, then the confidence level may be lowered. As another example, the object 42 may be detected to be approaching the limit of the electromagnetic field 38 and the confidence level 92 may be lowered in response. The proximity of the object 42 to the limit may be determined based on the location 58 determined by the magnetic tracking system 45, the secondary location 94 determined by the optical tracking system 74, and/or a known approximate limit of the base station 36 corresponding to factory calibrated settings, adjusted settings, and power input, for example.

F) Predict Future Pose and Display Computer Generated Image at Predicted Pose

Referring again to FIG. 1, the HMD device 10 will predict a future pose of an object (act 150) based in part on the pose data from the one or more tracking systems. In addition, a computer generated image is created, buffered, and displayed so that the user 31 of the HMD device 10 sees the computer generated image in correspondence to the pose of the real world object at that point in time (act 160).

Figure 17:
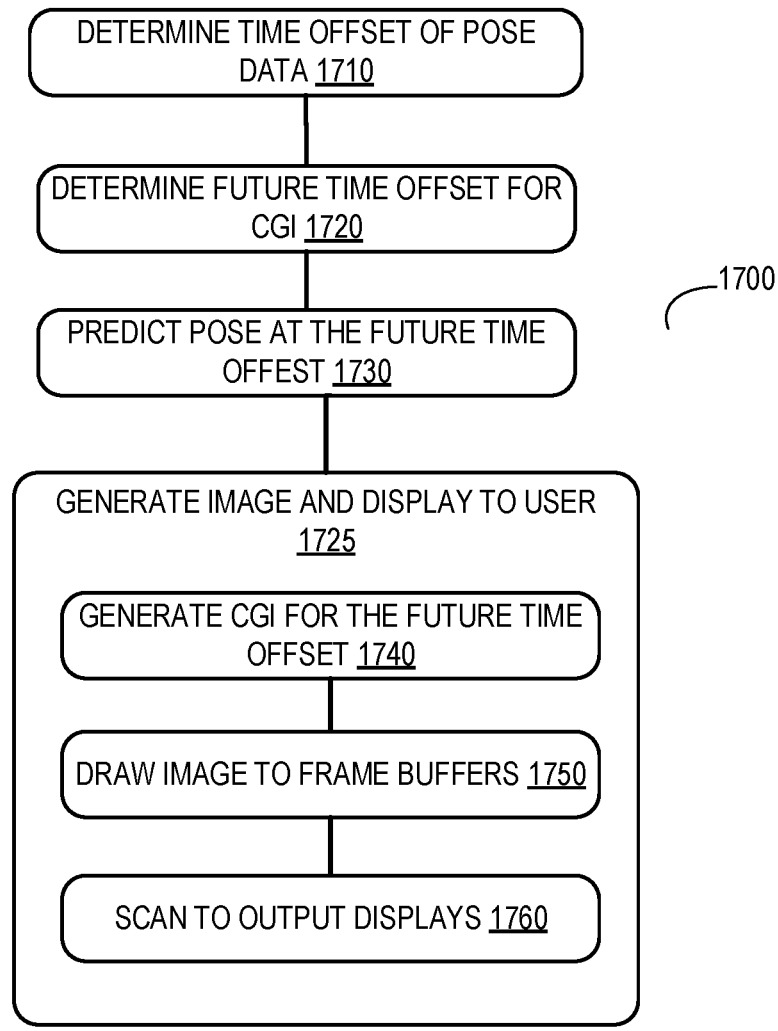
FIG. 17 shows a flowchart for a method to draw and render an image to a user.

FIG. 17 illustrates a method 1700 to create and display the correct image at the correct time and at the correct location and orientation for the CGI. It will be appreciated that the method 1700 may also be performed in other contexts using other suitable components.

With reference to FIG. 17, at 1710, the method 1700 may determine the time offset which represents the amount of time that has elapsed between the current clock time and the timestamp of the pose data. The pose data may be from the one or more tracking systems. Alternatively, the time offset may be determined by the homogenous data set. The time offset may be calculated as part of act 1710 or, alternatively, may be provided as part of the pose data set. The time offset from the pose data may be a relative time offset based on a common clock for the HMD 10, a clock time used by the processor 50A, 50B, or 50C, or other clock that may track the relative timing between the current time and the tracked pose data. Alternatively, the time offset may be based on a fixed delay sequence and the timing is a relative timing of the HMD 10.

At 1720, the method 1700 may include determining a future time offset that accounts for the time required to draw and render a specific image for the user to see (act 1725). The future time offset may be a fixed time interval based on known latency of the hardware and software configuration of the HMD 10. Alternatively, or additionally, the future time offset may calculated based on one or more factors that affect the time required to draw and render a specific image. For example, the image that is displayed may vary in complexity based on what needs to be rendered in the mixed reality system 100. Due in part to the complexity of the image to be created, the draw time may take more time or less time than a known average. To continue with this example and referring to FIG. 3, if the hologram 33 changes from being a glowing sword to a whip, the image of the whip needs to be generated. Before the change of the hologram 33 occurs, a model for the glowing sword may be partially or fully created enabling a faster image creation time of the glowing sword. However, when the hologram 33 is changed to a whip, the initial image creation time may take more time than when the same hologram type is used from image to image over time. This additional time to generate an image may be factored into the future time offset.

The future time offset of act 1720, may be additionally or alternatively affected by the variances in the time to draw and render the image. For example, the time to draw and render the same image could have variations that differ from 1-2 milliseconds to a full frame rate of 16 milliseconds or more. In such cases, the future time offset may account for these variations by anticipating the variations by using historical modeling data to determine an anticipated variation or by using identified factors, like low battery power, or exceeding defined thresholds in memory utilization to predict an expected variation in drawing and rendering an image. This variation may be included in the future time offset calculation.

At 1730, the method 1700 may include predicting the future pose of the real-world object at the determined time of the future time offset. The future pose may be based on the pose data set and the velocity and acceleration. The velocity and acceleration may be calculated from the pose data or may be captured by the tracking system and included in the pose data set.

The operations to generate the image and render the image to the user 31 may take a series of steps (act 1725). In one embodiment, the operations may include act 1740 where the image to be displayed at the future time is generated in part by the determined future pose and the future time offset. The image is then drawn to a frame buffer (act 1750). The frame buffer is scanned to the display (act 1760). As an alternative embodiment, the operations described may include projecting the image to a late-stage reprojection component.

Figure 18:
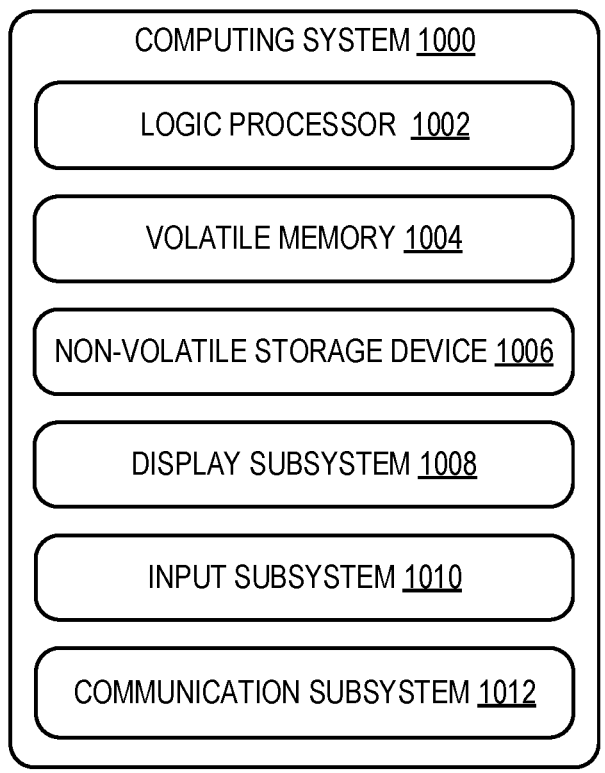
FIG. 18 shows a computing system according to an embodiment of the present description.

FIG. 18 schematically shows a non-limiting embodiment of a computing system 1000 that can enact one or more of the methods and processes described above. Computing system 1000 is shown in simplified form. Computing system 1000 may take the form of one or more head-mounted display devices as shown in FIG. 2, or one or more devices cooperating with a head-mounted display device (e.g., personal computers, server computers, tablet computers, home-entertainment computers, network computing devices, gaming devices, mobile computing devices, mobile communication devices (e.g., smart phone), the handheld input device 64, and/or other computing devices).

Computing system 1000 includes a logic processor 1002, volatile memory 1004, and a non-volatile storage device 1006. Computing system 1000 may optionally include a display subsystem 1008, input subsystem 1010, communication subsystem 1012, and/or other components not shown in FIG. 18.

Logic processor 1002 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 1002 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 1006 includes one or more physical devices configured to hold instructions executable by the logic processors to implement the methods and processes described herein. When such methods and processes are implemented, the state of non-volatile storage device 1006 may be transformed e.g., to hold different data.

Non-volatile storage device 1006 may include physical devices that are removable and/or built-in. Non-volatile storage device 1006 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 1006 may include nonvolatile, dynamic, static, read/write, read-only, sequential-access, location-addressable, file-addressable, and/or content-addressable devices. It will be appreciated that non-volatile storage device 1006 is configured to hold instructions even when power is cut to the non-volatile storage device 1006.

Volatile memory 1004 may include physical devices that include random access memory. Volatile memory 1004 is typically utilized by logic processor 1002 to temporarily store information during processing of software instructions. It will be appreciated that volatile memory 1004 typically does not continue to store instructions when power is cut to the volatile memory 1004.

Aspects of logic processor 1002, volatile memory 1004, and non-volatile storage device 1006 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 1000 implemented to perform a particular function. In some cases, a module, program, or engine may be instantiated via logic processor 1002 executing instructions held by non-volatile storage device 1006, using portions of volatile memory 1004. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 1008 may be used to present a visual representation of data held by non-volatile storage device 1006. This visual representation may take the form of a graphical user interface (GUI). As the herein described methods and processes change the data held by the non-volatile storage device, and thus transform the state of the non-volatile storage device, the state of display subsystem 1008 may likewise be transformed to visually represent changes in the underlying data. Display subsystem 1008 may include one or more display devices utilizing virtually any type of technology. Such display devices may be combined with logic processor 1002, volatile memory 1004, and/or non-volatile storage device 1006 in a shared enclosure, or such display devices may be peripheral display devices. The at least partially opaque or see-through display of HMD device 10 described above is one example of a display subsystem 1008.

When included, input subsystem 1010 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; any of the sensors described above with respect to position sensor system 28 of FIG. 2; and/or any other suitable sensor.

When included, communication subsystem 1012 may be configured to communicatively couple computing system 1000 with one or more other computing devices. Communication subsystem 1012 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1000 to send and/or receive messages to and/or from other devices via a network such as the Internet.

The subject matter of this disclosure is further described in the following paragraphs. One aspect provides a system for tracking the pose of a real-world object in a mixed reality system, the system comprising a head-mounted display (HMD) device. The system may further comprise a magnetic tracking system configured to capture location data of the object, the magnetic tracking system comprising a base station configured to emit an electromagnetic field (EMF), and an EMF sensor configured to sense the EMF. The system may further comprise a second tracking system configured to capture tracking data of the object. The system may include a processor configured to determine the pose of the object based in part on the location data from the magnetic tracking system and the tracking data from the second tracking system where the location data from the magnetic tracking system and the tracking data from the second tracking system are synchronized by time. In this aspect, a timestamp may be used to correlate location data from the magnetic tracking system with tracking data detected by the second tracking system and the timestamp of the magnetic tracking system is embedded in the electromagnetic field. In this aspect, the data from the second tracking system may be used to disambiguate the pose data from the magnetic tracking system. In this aspect, the base station may comprise two or more coils and the EMF sensor may comprise three substantially orthogonal coils. In this aspect, the second tracking system may comprise an optical tracking system. In this aspect, the optical sensor may detect a reflective marker. In this aspect, the data from the optical tracking system may be timestamped from a clock on the HMD. In this aspect, the timestamp correlating to the location data from the magnetic tracking system may be determined by a clock on the HMD and a clock on the object. In this aspect, the base station may be mounted to the object and the EMF sensor may be affixed to the HMD device. In this aspect, the second tracking system may comprise an IMU attached to the object.

According to another aspect, a method for tracking the pose of a real-world object in a mixed reality system comprising tracking the location of the object using a magnetic tracking system where the magnetic tracking system comprises a base station configured to emit an electromagnetic field (EMF), and an EMF sensor configured to sense the EMF where the location data for the magnetic tracking system is captured. The method may further comprise tracking the object using a second tracking wherein tracking data is captured. The method may further comprise calculating the pose of the object based in part from the location data from the magnetic tracking system and the tracking data from the second tracking system where the location data from the magnetic tracking system and the tracking data from the second tracking system may be synchronized by time. In this aspect, a timestamp may be used to correlate the location data from the magnetic tracking system with tracking data detected by the second tracking system and the timestamp of the magnetic tracking system may be embedded in the electromagnetic field. In this aspect, the data from the second tracking system may disambiguate the pose data from the magnetic tracking system. In this aspect, the base station may comprise two or more coils and the EMF sensor may comprise three substantially orthogonal coils. In this aspect, the second tracking system may comprise an optical tracking system. In this aspect, the optical sensor may detect a reflective marker. In this aspect, the tracking data from the optical tracking system may be timestamped from a clock on the HMD. In this aspect, the base station may be mounted to the object and the EMF sensor may be affixed to the HMD device. In this aspect, the timestamp correlating to the location data from the magnetic tracking system may be determined by a clock on the HMD and a clock on the object. In this aspect, the second tracking system may comprise an IMU attached to the object.

According to another aspect, a system for displaying, within a mixed reality system display, a computer generated image corresponding to the pose of a real-world object located within a real-world environment comprising a head-mounted display (HMD) device that includes a display rendering system having a time offset based on the time needed to calculate, buffer and generate display output. The HDM may include a first tracking system configured to track the location of the real world object, a second tracking system configured to track the real world object, and a processor configured to calculate a future pose of the real world object based in part on the time offset and location data from the first tracking system, the time offset and tracking data from the second tracking system, and the time offset from the display rendering system such that the relative location of the computer generated image (CGI) corresponds with the actual location of the real-world object relative to the real world environment at the time the CGI actually appears in the mixed reality display. In this aspect, the first tracking system may be a magnetic tracking system where the timestamp correlated to the location data from the magnetic tracking system may be determined by modulating the electromagnetic field to embed a timestamp. In this aspect, the data from the second tracking system may disambiguate the location data from the magnetic tracking system. In this aspect, the base station may comprise two or more coils and the EMF sensor may comprise three substantially orthogonal coils. In this aspect, the base station may be mounted to the object and the EMF sensor may be affixed to the HMD device. In this aspect, the timestamp correlating to the location data from the magnetic tracking system may be determined by a clock on the HMD and a clock on the object. In this aspect, the second tracking system may comprise an optical tracking system. In this aspect, an optical sensor may detect a reflective marker. In this aspect, the pose data from the optical tracking system may be determined by a clock on the HMD. In this aspect, the second tracking system may comprise an IMU attached to the object.

According to another aspect, a method for displaying, within a mixed reality system, a computer generated image (CGI) corresponding to the pose of a real-world object located within a real-world environment comprising determining a future point in time when the image will be seen by a user wherein the future point in time is in part determined by an expected time offset to calculate, buffer and generate a display output. The method may further comprise determining a future pose of the real-world object wherein the pose is determined from pose data from one or more tacking systems where pose, velocity, and acceleration can be determined, and a known time offset for the one or more tracking system data, and the determined future point in time the image is displayed to the user. The method may further comprise displaying the computer generated image such that the location of the CGI within the mixed reality display is synchronized, at the time the CGI appears in the mixed reality display, corresponding to the pose of the real-world object relative to the real world environment. In this aspect, the pose data may be in part determined from location data from a magnetic tracking system where the base station may comprise two or more coils and the EMF sensor may comprise three substantially orthogonal coils. In this aspect, the timestamp correlated to the location data from the magnetic tracking system may be determined by modulating the electromagnetic field to embed a timestamp. In this aspect, the timestamp correlating to the location data from the magnetic tracking system may be determined by a clock on the HMD and a clock on the object. In this aspect, the base station may be mounted to the object and the EMF sensor may be affixed to the HMD device. In this aspect, the pose may be determined in part from a second tracking system used to disambiguate the location data from the magnetic tracking system. In this aspect, the second tracking system a comprise an optical tracking system. In this aspect, an optical sensor may detect a reflective marker. In this aspect, the pose data from the optical tracking system may be determined by a clock on the HMD. In this aspect, the second tracking system may comprise an IMU attached to the object.

According to another aspect, a system for displaying a computer generated image corresponding to the pose of a real-world object in a mixed reality system comprising a head-mounted display (HMD) device that may include a display rendering system having a time offset based on the time needed to calculate, buffer and generate display output. The system may further comprise a magnetic tracking system configured to capture location data of the object comprising a base station configured to emit an electromagnetic field (EMF), and an EMF sensor configured to sense the EMF. The system may further comprise a second tracking system configured to capture tracking data of the object. The system may further comprise the location data derived from the magnetic tracking system and the tracking data derived from the second tracking system are synchronized in time. The system may include a processor configured to calculate a future pose of the real world object based in part on the time offset and location data from the magnetic tracking system, the time offset and tracking data from the second tracking system, and the time offset from the display rendering system such that the relative location of the computer generated image (CGI) corresponds with the actual location of the real-world object relative to the real world environment at the time the CGI actually appears in the mixed reality display. In this aspect, the timestamp correlated to the location data from the magnetic tracking system may be determined by modulating the electromagnetic field to embed a timestamp. In this aspect, the data from the second tracking system may disambiguate the location data from the magnetic tracking system. In this aspect, the base station may comprise two or more coils and the EMF sensor may comprise three substantially orthogonal coils. In this aspect, the second tracking system may comprise an optical tracking system. In this aspect, an optical sensor may detect a reflective marker. In this aspect, the pose data from the optical tracking system may be determined by a clock on the HMD. In this aspect, the base station is mounted to the object and the EMF sensor may be affixed to the HMD device. In this aspect, the timestamp correlating to the location data from the magnetic tracking system may be determined by a clock on the HMD and a clock on the object. In this aspect, the second tracking system may comprise an IMU attached to the object.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

What is claimed is:

1. A system for displaying, within a mixed reality system display, a computer generated image corresponding to the pose of a real-world object located within a real-world environment, the system comprising:
a head-mounted display (HMD) device that includes a display rendering system;
a first tracking system configured to provide location data of the real world object;
a second tracking system configured to provide tracking data of the real world object; and
one or more processors configured to:
determine a first time offset based on an amount of time that has elapsed between a current clock and one or more timestamps indicating when the location data and the tracking data were provided,
determine a second time offset based on the time needed for the display rendering system to calculate, buffer and generate display output, and
calculate a future pose of the real-world object based in part on:
the location data of the real-world object,
the tracking data of the real-world object,
the first time offset, and
the second time offset from the display rendering system such that the relative location of the computer generated image (CGI) corresponds with the actual location of the real-world object relative to the real world environment at the time the CGI actually appears in the mixed reality display.

2. The mixed reality system of claim 1, wherein the first tracking system is a magnetic tracking system, wherein a timestamp is used to correlate location data from the magnetic tracking system with tracking data detected by the second tracking system, and wherein the timestamp correlated to the location data from the magnetic tracking system is determined by modulating the electromagnetic field to embed a timestamp.

3. The mixed reality system of claim 2, wherein the data from the second tracking system disambiguates the location data from the magnetic tracking system.

4. The mixed reality system of claim 2, wherein the base station comprises of two or more coils and the EMF sensor comprises of three substantially orthogonal coils.

5. The mixed reality system of claim 2, wherein the base station is mounted to the object and the EMF sensor is affixed to the HMD device.

6. The mixed reality system of claim 1, wherein the timestamp correlating to the location data from the magnetic tracking system is determined by a clock on the HMD and a clock on the object.

7. The mixed reality system of claim 1, wherein the second tracking system comprises an optical tracking system.

8. The mixed reality system of claim 7, wherein an optical sensor detects a reflective marker.

9. The mixed reality system of claim 7, wherein the pose data from the optical tracking system is determined by a clock on the HMD.

10. The mixed reality system of claim 1, wherein the second tracking system comprises an IMU attached to the object.

11. A method for displaying, within a mixed reality system, a computer generated image (CGI) corresponding to the pose of a real-world object located within a real-world environment, the method comprising:
determining a future point in time when the image will be seen by a user wherein the future point in time is in part determined by an expected time to calculate, buffer and generate a display output;
determining a future pose of the real-world object wherein the pose is determined from:
pose data from two or more tacking systems where pose, velocity, and acceleration can be determined; and
a known time offset for the pose data from the two or more tracking systems based on an amount of time that has elapsed between a current clock and one or more timestamps indicating when the pose data was determined, and
the determined future point in time the image is displayed to the user; and
displaying the computer generated image such that the location of the CGI within the mixed reality display is synchronized, at the time the CGI appears in the mixed reality display, corresponding to the pose of the real-world object relative to the real world environment.

12. The method of claim 11, wherein the pose data is in part determined from location data from a magnetic tracking system where the base station comprises of two or more coils and the EMF sensor comprises of three substantially orthogonal coils.

13. The method of claim 12, wherein a timestamp is used to correlate location data from the magnetic tracking system with tracking data detected by the second tracking system, and wherein the timestamp correlated to the location data from the magnetic tracking system is determined by modulating the electromagnetic field to embed a timestamp.

14. The method of claim 12, wherein the timestamp correlating to the location data from the magnetic tracking system is determined by a clock on the HMD and a clock on the object.

15. The method of claim 12, wherein the base station is mounted to the object and the EMF sensor is affixed to the HMD device.

16. The method of claim 12, wherein the pose is in part determined from a second tracking system used to disambiguate the location data from the magnetic tracking system.

17. The method of claim 16, wherein the second tracking system comprises an optical tracking system.

18. The method of claim 17, wherein an optical sensor detects a reflective marker.

19. The method of claim 17, wherein the pose data from the optical tracking system is determined by a clock on the HMD.

20. The method of claim 16, wherein the second tracking system comprises an IMU attached to the object.

21. A system for displaying a computer generated image corresponding to the pose of a real-world object in a mixed reality system, the system comprising:

a head-mounted display (HMD) device that includes a display rendering system having a first time offset based on the time needed to calculate, buffer and generate display output;
a magnetic tracking system configured to capture location data of the object, the magnetic tracking system comprising:
a base station located at a predetermined fixed position relative to the HMD, the base station being configured to emit an electromagnetic field (EMF); and
an EMF sensor configured to sense the EMF;
a second tracking system configured to capture tracking data of the object,
wherein the location data derived from the magnetic tracking system and the tracking data derived from the second tracking system are synchronized in time; and
one or more processors configured to:
determine a second time offset based on an amount of time that has elapsed between a current clock and a timestamp indicating when the location data and the tracking data were captured, and
calculate a future pose of the real-world object based in part on:
the location data from the magnetic tracking system,
the tracking data from the second tracking system,
the first time offset from the display rendering system, and the second time offset
such that the relative location of the computer generated image (CGI) corresponds with the actual location of the real-world object relative to the real world environment at the time the CGI actually appears in the mixed reality display.

* * * * *